US008298793B2

(12) United States Patent
Vodyanoy et al.

(10) Patent No.: US 8,298,793 B2
(45) Date of Patent: *Oct. 30, 2012

(54) METHODS FOR ISOLATING PROTEONS FROM PLASMA SAMPLES

(75) Inventors: Vitaly J. Vodyanoy, Auburn, AL (US); Alexandre M. Saamoylov, Auburn, AL (US); Oleg M. Pustovyy, Auburn, AL (US)

(73) Assignee: Auburn University, Auburn, AL (US)

( * ) Notice: Subject to any disclaimer, the term of this patent is extended or adjusted under 35 U.S.C. 154(b) by 714 days.

This patent is subject to a terminal disclaimer.

(21) Appl. No.: 11/523,250

(22) Filed: Sep. 19, 2006

(65) Prior Publication Data

US 2007/0122799 A1 May 31, 2007

Related U.S. Application Data

(63) Continuation-in-part of application No. 10/674,750, filed on Sep. 30, 2003, now Pat. No. 7,138,255.

(60) Provisional application No. 60/415,108, filed on Sep. 30, 2002, provisional application No. 60/792,241, filed on Apr. 14, 2006.

(51) Int. Cl.
*C12P 19/34* (2006.01)
(52) U.S. Cl. ........ 435/91.2; 530/350; 435/7.1; 435/68.1
(58) Field of Classification Search ........................ None
See application file for complete search history.

(56) References Cited

U.S. PATENT DOCUMENTS 5,874,238 A 2/1999 Potempa et al.
7,138,255 B2 11/2006 Vodyanoy et al.

FOREIGN PATENT DOCUMENTS

WO 96/37282 A1 11/1996
WO WO 02/073210 A 9/2002

OTHER PUBLICATIONS

Houston et al. Lancet. Sep. 16, 2000;356(9234):999-1000.*
Shaked et al. J Virol. Sep. 2001;75(17):7872-4.*
Lisiecki et al. Journal of Molecular Liquids. 1997; 72:251-261.*
Samoylov et al. 2005. Cells Tissues Organs. Novel Metal Clusters Isolatedfrom Blood are Lethal to Cancer Cells. 179: 115-124.*
Saborio Gabriela et al. (2001)"Sensitive Detection of Pathological Prion Protein by Cyclic Amplification of Protein Misfolding" *Nature*, Nature Publishing Group, London GB, vol. 411, No. 6839.
Rataboul et al. (2002)"Synthesis and Characterization of Monodisperse Zinc and Zinc Oxide Nanoparticles from the Organmetallic Precursor [Zn(C6H11)2]" *Journal of Organometallic Chemistry*, Elsevier-Sequoia S.A. Lausanne, CH, vol. 643-644.
Rivas et al. (1993) "First Steps Towards Tailoring Fine Andultrafine Iron Particles Using Microemulsions," *IEE Transactions on Magnetics*, IEEE Service Center, New York, NY, US, vol. 29, No. 6.
Kapoor et al. (2000)"Laser-induced fragmentation and melting of cadmium and copper nanoparticles" *Materials Research Bulletin*, Elsevier, Kidlington, GB, vol. 35, No. 13.
(1997) "In-situ Observations of Classical Grain Growth Mechanisms During Sintering of Copper Nanoparticles on (001) Copper," *Applied Physics Letters*, AIP, American Institute of Physics, Melville, NY, US, vol. 71, No. 12.
Enderlein, Gunther (Prof., Dr.), "Bacteria Cyclogeny", pp. 27-39; published in German 1916, 1981 (translated Jan. 1999).
Ursini, Fulvio, et al, "Atherosclerosis: Another Protein Misfolding Disease?", TRENDS in Molecular Medicine, vol. 8, No. 8, pp. 370-374, Aug. 2002.
Wetterberg, Lennart, et al "Micrometer-Sized Particles in Cerebrospinal Fluid (CSF) in Patients with Schizophrenia", Neuroscience Letters, 329 (2002) pp. 91-95.
Schluter, Karen and Drenckhahn, Detlev, "Co-Clustering of Denatured Hemoglobin with Band 3: Its Role in Binding of Autoantibodies Against Band 3 to Abnormal and Aged Erythrocytes", Medical Sciences, Proc. Natl. Acad. Sci. USA, vol. 83, pp. 6137-6141, Aug. 1986.
Prusiner, Stanley B., "Molecular Biology of Prion Diseases", Science, vol. 252, Jun. 14, 1991, pp. 1515-1522.
Soto, Claudio, "Protein Misfolding and Disease; Protein Refolding and Therapy", FEBS Letters, 498 (2001) pp. 204-207.
Wille, Holger, et al, "Structural Studies of the Scrapie Prion Protein by Electron Crystallography", PNAS, vol. 99, No. 6, Mar. 19, 2002, pp. 3563-3568.
Geschwind, Michael D. (M.D., Ph.D.), et al, "Challenging the Clinical Utility of the 14-3-3 Protein for the Diagnosis of Sporadic Creutzfeldt-Jakob Disease", Arch Neurol, vol. 60, Jun. 2003, pp. 813-816.
Kannan, Rama, et al, "Isolation and Characterization of the Hemichrome-Stabilized Membrane Protein Aggregates from Sickle Erythrocytes", The Journal of Biological Chemistry, vol. 263, No. 27, Issue of Sep. 25, 1988, pp. 13766-13773.
Jaikaran, Emma T. A. S. and Clark, Anne, "Islet Amyloid and Type 2 Diabetes: From Molecular Misfolding to Islet Pathophysiology", Biochimica et Biophysica Acta, 1537 (2001) pp. 179-203.
Rahman, Qamar, et al, "Evidence That Ultrafine Titanium Dioxide Induces Micronuclei and Apoptosis in Syrian Hamster Embryo Fibroblasts", Environmental Health Perspectives, vol. 110, No. 8, Aug. 2002, pp. 797-800.
Wille, Holger, et al, "Structural Studies of the Scrapie Prion Protein by Electron Crystallography", Biophysical Journal, vol. 82, Issue 1, p. 169A, Part 2 Meeting; Abstract, p. 825, published Jan. 2002.

(Continued)

*Primary Examiner* — Zachariah Lucas
*Assistant Examiner* — Michelle S Horning
(74) *Attorney, Agent, or Firm* — Andrus, Sceales, Starke & Sawall, LLP

(57) ABSTRACT

Compositions and methods for the isolation and manipulation of misfolded, or partially misfolded, proteins present in blood and other biological materials are provided. In one aspect of the invention, the compositions, hereinafter termed "proteons" are misfolded or partially misfolded proteins surrounding a metallic nanocluster, termed "proteon nucleation center" (PNC). Also provided are compositions and methods for the isolation and manipulation of proteon nucleation centers (PNCs) upon which the proteons of the present in blood and other biological materials form.

10 Claims, 7 Drawing Sheets

OTHER PUBLICATIONS

Figure 1:
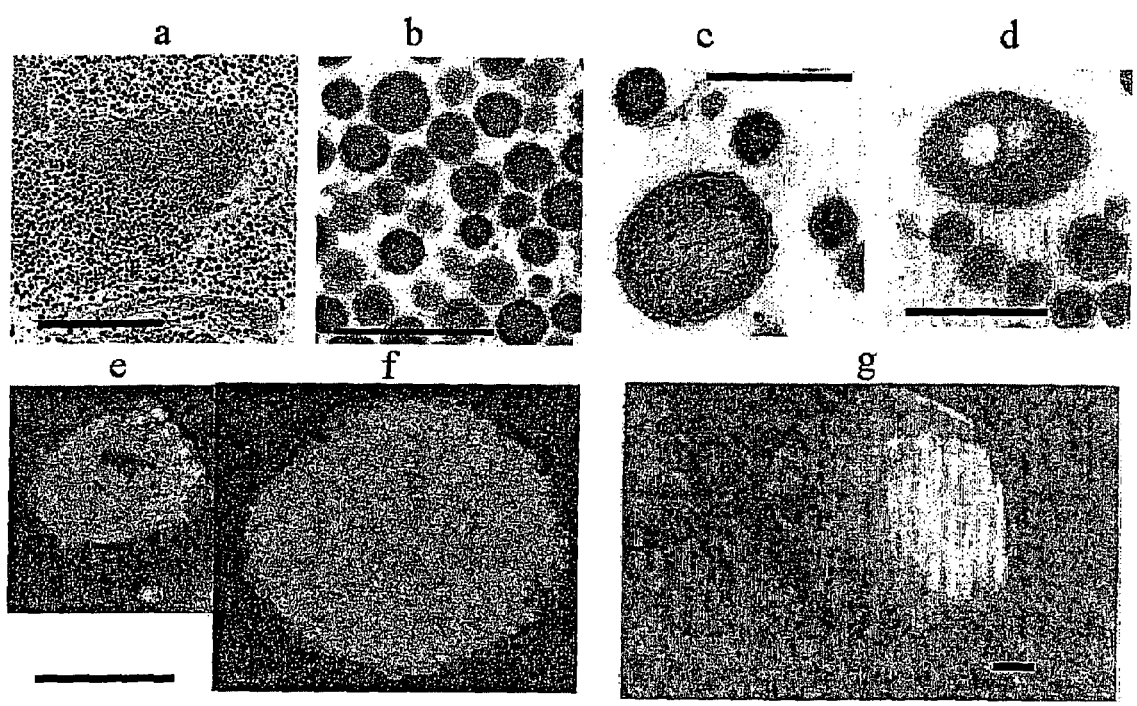

Dyson, H. Jane, "Structure and Dynamics of Prion and Doppel Proteins", Biophysical Journal, vol. 82, Issue 1, p. 169A, Part 2 Meeting; Abstract, p. 824, published Jan. 2002.

Aguzzi, A., Prion diseases, blood and the immune system: concerns and reality; Haematologica, Jan. 2000, pp. 3-10, vol. 85, No. 1.

Aguzzi, A., Blood simple prion diagnostics; nature Medicine, Mar. 2001, pp. 289-290, vol. 7, No. 3.

Aiken III, J.D. and Finke, R.G., A review of modern transition-metal nanoclusters: their synthesis, characterization, and applications in catalysis, Journal of Molecular Catalysis A: Chemical, 1999, pp. 1-44, vol. 145.

Attwood, T.K., Metals in prion disease, Trends in Biotechnology, Jun. 2002, p. 235, vol. 20, No. 6.

Brown, P. et al, Blood infectivity and the prospects for a diagnostic screening test in Creutzfeldt-Jakob disease; J. Lab. Clin. Med., 2001, pp. 5-13, vol. 137.

Bush, A.I., Metals and neuroscience; Current opinions in Chemical Biology, 2000, pp. 184-191, vol. 4.

Bush, A.I. et al, Rapid Induction of Alzheimer A Beta Amyloid Formation by Zinc, Science, Sep. 1994, pp. 1464-1467, vol. 265, No. 5177.

Bush, A.I., Metal complexing agents as therapies for Alzheimer's disease, Neurobiology of Aging, 2002, pp. 1031-1038, vol. 23.

Campbell, Arezoo et al, Mechanisms by which metals promote events connected to neurodegenerative diseases, Brain Research Bulletin, 2001, pp. 125-132, vol. 55, No. 2.

Carrell R.W. et al, Conformational disease, Lancet, Jul. 12, 1997, pp. 134-138, vol. 350.

Gerner, Christopher, Biochemische Analyse endobiontischer Strukturen aus dem menshlichen Blut, [Biochemical Analysis of Endobiontic Structures from Human Blood], Curriculum Oncologicum 01, Jan. 7, 1997.

Harper, James D. and Lansbury, Peter T., Models of amyloid seeding in Alzheimer's disease and scrapie: mechanistic truths and physiological consequences of the time-dependent solubility of amyloid proteins, Ann. Rev. Biochem., 1997, pp. 385-407, vol. 66.

Lehmann, Sylvain, Metal ions and prion diseases, Current Opinion in Chemical Biology, 2002, pp. 187-192, vol. 6.

Liu, C. and Xu, H., The metal site as a template for the metalloprotein structure formation, Journal of Inorganic Biochemistry, 2002, pp. 77-86, vol. 88.

Otvos, J.D. et al, Structure of the metal clustesr in rabbit liver metallothionein, Proc. Natl. Acad. Sci USA, Dec. 1980, pp. 7094-7098, vol. 77, No. 12.

Rhoades, E. et al, Aggregation of an amyloidogenic fragment of human islet amyloid polypeptide, Biochemica et Biophysica Acta, 2000, pp. 230-238, vol. 1476.

Soto, C. et al, Cyclic amplification of protein misfolding: application to prion-related disorders and beyond, Trends in Neurosciences, Aug. 2002, pp. 390-394, vol. 25, No. 8.

Thackray, A.M. et al, Metal imbalance and compromised antioxidant function are early changes in prior disease, Biochem. J., 2002, pp. 253,258, vol. 362.

Watanabe et al, Inhibition against Heat Coagulation of Ovotransferrin by Ovalbumin Dry-Heated at 120 Degrees C, J. Agric Food Chemic., Sep. 2002, 48(9), pp. 3965-3963.

* cited by examiner

METHODS FOR ISOLATING PROTEONS FROM PLASMA SAMPLES

CROSS REFERENCE TO RELATED APPLICATIONS

This application is a continuation-in-part of U.S. patent application Ser. No. 10/674,750, now U.S. Pat. No. 7,138,255, and claims the benefit of U.S. Provisional Application Ser. No. 60/415,108 filed on Sep. 30, 2002, and U.S. Provisional Application Ser. No. 60/792,241 filed Apr. 14, 2006 which are hereby incorporated in their entirety by reference herein.

FIELD OF THE INVENTION

The present invention relates generally to compositions and methods for the isolation and manipulation of misfolded proteins and their nucleation centers.

BACKGROUND OF THE INVENTION

There are many disorders that are though to arise from the same general mechanism based upon misfolding and aggregation of underlying proteins, including prion-related disorders, neurodegenerative diseases, and several systemic disorders. See, for example, Schluter et al. (1986) PNAS 83:6137-6141; Kannan et al. (1988) J. Biol. Chem. 263:3766-13773; Carrell and Lomas (1997) Lancet 350:134-138; Carrell and Gooptu (1998) Curr. Op. Struc. Biol. 8:799-809; Soto (2001) FEBS Letters 498:204-207; Jaikaran and Clark (2001) Biochimica et Biophysica Acta 1537:179-203; Ursini et al. (2002) Trends Mol. Med. 8:370-374; and Davis et al. (2002) Lancet 359:2242-2247.

One of the suggested mechanisms of protein aggregation is seeded polymerization, in which initial seeds nucleate the deposition of monomers. For example, aggregates of denatured hemoglobin called Heinz bodies were found in aged erythrocytes. See Schluter et al. (Supra). Further, Kannan et al (Supra) described a protein aggregation from sickle erythrocytes that is mostly composed of blogin. Particles resembling those described by Enderlein (1925 Bakterien-Cyclogenie (Verlag de Gruyter & Co, Berlin), were isolated from the blood of cancer patients and determined to be composed of mainly denatured hemoglobin (Gemer (1997) Blut. Curr. Onkol. 7:6P12).

Aggregated proteins associated with disorders are found in other biological materials, as well. For example, proteinaceous particles isolated from brain were identified as causing scrapie (Prusiner, (1982) Science 216:136-144). Since then, these particles and their structure have represented important areas of study (Prusiner (1991) Science 252:1515-1522; Wille et al. (2002) Biophysical J. 82:825; Wille et al. (2002) PNAS 99:3563-3568; Geschwind et al. (2002) Neurology 58:A135-A135; Dyson et al. (2002) Biophysical J. 82:825), and methods for the sensitive detection of prion-related disorders using ultrasound have been developed. Se Saborio (2001) Nature 411:810-813. Recently, micrometer-sized particles were identified in the cerebrospinal fluid of patients with schizophrenia (Wetterberg et al. (2002) Neurosci Lett. 329:91-5). Accordingly, new compositions and methods for the formation, isolation, and detection of misfolded, aggregated proteins are required.

SUMMARY OF THE INVENTION

Compositions and methods for the isolation and manipulation of misfolded, or partially misfolded, proteins in blood and other biological materials are provided. In one aspect of the invention, the compositions, hereinafter termed "proteons," include misfolded proteins and/or partially misfolded proteins surrounding a PNC. Also provided are compositions and methods for the isolation and manipulation of proteon nucleation centers (PNCs), upon which the proteons of the present invention form. The PNCs are metallic nanoclusters.

Proteons can be visualized by microscopy of biological materials, for example fluids such as blood samples of mammals and homogenates of vegetable matter. As proteons include misfolded proteins, detection of proteons and identification of proteins can be used to diagnose and measure progression of disease states. For example, proteons isolated and purified from blood and blood plasma lack detectable nucleic acids, but contain two major polypeptide populations with high homology to the alpha chain of hemoglobin.

Accordingly, methods for the amplification and detection of misfolded protein in a biological sample are provided. Additionally, methods for the clearance of misfolded protein from a sample of biological material are provided. The method can be manipulated by subjecting the sample to heat or pressure, or by carrying out various numbers of seeding steps. Methods for amplification include heat and pressure treatment of a sample. Likewise, subjecting a biological sample to or treating it with metal clusters increases the concentration of proteons.

Preferably, the method for cleaning misfolded proteins from a biological sample such as blood comprises contacting the sample with a proteon nucleation center (PNC) for a period of time, said proteon nucleation center (PNC) comprising a metallic nanoparticle having a diameter of about 1-2 nm and containing about 40-300 metal atoms selected from the group consisting of copper, zinc, or iron, and removing the misfolded proteins from the sample.

The method for cyclic amplification of proteons in a biological sample preferably comprises the steps of: a) placing an aliquot of a sample containing a proteon nucleation center (PNC) in an unheated subsample, said proteon nucleation center (PNC) comprising metallic nanoparticle having a diameter of about 1-2 nm and containing about 40-300 metal atoms selected from the group consisting of copper zinc, iron and alloys of copper, zinc or iron; b) heating the subsample, and c) determining the number of proteons in said sample, said proteons comprised of misfolded or partially misfolded proteins surrounding a proteon nucleation center (PNC); and (d) repeating steps (a), (b) and (c) with aliquots taken from the most recently heated subsample for 1 or more cycles until the number of proteons determined to be in each heated subsample no longer increases.

Methods for the detection of disorders are also provided. The first method involves the use of an antibody. The antibody can recognize prion-proteins and distinguish between prions that are misfolded and prion-proteins that are normal. However, the number of misfolded proteins is typically very small making detection of misfolded proteins very difficult. As a result cyclic amplification is performed to increase the number of misfolded proteins and then the antibody is used. The second method, which also involves cyclic amplification, recognizes that there are certain prion proteins in blood. Thus, after cyclic amplification, this method adds enzymes to blood containing the prion proteins to digest the prion proteins, and thereafter filter and remove the PNCs.

More specifically, the method for the detection of a disorder using an antibody comprises the steps of: a) centrifuging a biological sample until a supernatant is formed; b) dividing said supernatant into a plurality of subsamples; c) heating a subsample; d) obtaining an aliquot of said heated subsample;

e) placing said aliquot into an unheated subsample; f) heating the subsample of (e); and g) repeating steps d-f with aliquots taken from the most recently heated subsample for 1 or more cycles to produce a final subsample; h) contacting said final subsample with an antibody that binds to a protein selected from the group consisting of hemoglobin, prion protein, β-amloid, α-synuclein, tau protein, serpins, neuroserpin, glutamate repeats, amylin, SOD, ApoB CFTR protein, immunoglobulin, amyloid light chain, serum amyloid A, transthyretin, β2-microglobulin, apolipoprotein A-1, cystatin C, lysozyme, prion protein fragments, beta protein fragment 1-40/43, immunoglobulin light chain or fragments thereof, serum amyloid A 78 residue fragment, transthyretin fragments, apolipoprotein A-1 fragments, cystatin A minus 10 residues, gelsolin 71 residue, islet amyloid polypeptide fragment, insulin, calcitonin fragments, atrial natriuretic factor, lysozyme and fragments thereof, and fibrinogen fragments; i) identifying the protein; and j) correlating the identified protein to a disorder selected from the group consisting of sickle cell anemia, the presence of Heinz bodies, inclusion body hemolysis, drug-induced inclusion body hemolysis, cancer, atherosclerosis, malaria, infections, auto-immune disorders, toxic reactions, internal bleeding, Creutzfeld-Jacob disease (CJD), new variant CJD, bovine spongiform encephalopathy (BSE), Gerstmann-Straussler-Schheinker disease, fatal familial insomnia, kuru, Alzheimer's disease, Down's syndrome, familial Alzheimer's disease, Parkinson's disease, the presence of Lewy bodies, frontotemporal dementia, the presence of Pick bodies, α1-antitrypsin deficiency, cirrhosis, emphysema, antithrombin deficiency, thrombosis, C1-inhibitor deficiency, angioedema, neurodegenerative disease, the presence of Collins bodies, inherited neurodegenerative disorders, Huntington's disease, diabetes type II, amyotrophic lateral sclerosis, atherosclerosis, cystic fibrosis, systemic amyloid light chain amyloidosis, nodular amyloidosis, reactive systemic amloid A amloidoses, chronic inflammatory disease, senile systemic amloidosis, familial amyloid neuropathy, familial cardiac amyloidosis, hemodialysis amyloidosis, the presence of prostatic amyloid, familial amyloid polyneuropathy, familial visceral amyloidosis, hereditary (Icelandic) cerebral angiopathy, familial visceral amyloidosis, spongiform encephalopathies, primary systematic amloidosis, secondary systematic amyloidosis, familial amyloid polyneuropathy I, familial amyloid polyneuropathy III, cerebral amyloid angiopathy, Finnish hereditary systemic amyloidosis, injection-localized amyloidosis, medullary thyroid carcinoma, atrial amyloidosis, non-neuropathic systemic amylodosis, and hereditary renal amyloidosis.

The method using an enzyme is similar in that it also employs the above cyclic amplification steps (a) through (g). However, a digestive enzyme is then added to digest any normal prion proteins so that only misfolded prion proteins remain. Thereafter, an antibody that is non-specific and that binds only to the prions i.e. misfolded prion proteins, is added. The remaining identification and correlation steps are then also performed.

While the present invention is not bound to any particular mode of action, it is believed that proteons are formed by a mechanism involving the reversible polymerization and aggregration of proteins, particularly misfolded proteins, on a nucleation center. For convenience, the nucleation centers are referred to as "proteon nucleation centers" or PNCs."

The PNCs of the invention are unexpectedly pro-apoptotic when added to cultured animal cells. Accordingly, pro-apoptotic compositions and methods for their production are also provided herein.

In a particularly useful embodiment, the present invention provides a method for the isolation, containment and destruction of disease causing prions and proteons, particularly infectious agents of Bovine Spongiform Encephalopathy (BSE) and other infectious disease. The method comprises 1) treatment of the causative prions or proteons with protein denaturing agents which unfolds and/or changes the protein structure of the prions or proteons to render the metal components of the prions or proteons subject to chelation by suitable ligands. Such denaturants include urea, guanidinium salts, trimethylamine N-oxide, and certain sugars; 2) the addition of chelating agents to the unfolded prions or proteons to immobilize the Protein Nucleation Center (PNC) and destroy the functionality or infective properties of the prions/proteons. Such chelating agents include the class of aminopolycarboxylates such as EDTA, EDPA, NTA, and others; 3) treatment with aerobic and anaerobic proteases to digest non-bound prion protein; and 4) final treatment with creosote or other disinfectants such as chlorine and other biocides.

The method of the present invention may also be applied to the treatment of cancer by first adding PNC and/or proteons to a group of cancer cells. Next, adding chelating agents in order to homogenize the solution, and then adding proteases to digest the proteins but not the PNCs. This process would eliminate the misfolded proteins that cause the cancerous cells without digesting the PNCs. The method may be altered or adjusted in accordance with the particular treatment application desired.

This invention has significant potential value in the control of mad cow disease and other prion/proteon medicated diseases in animals and man. The invention may be used to control mad cow disease or other pathogenic proteons causing conformational diseases; modulators of the immune system; regulation of protein turnover; regulation of pathogenic proteons and control of conformational disease by regulating assembling and disassembling of pathogenic proteons.

The invention provides methods of fast and efficient production of small protein particles (proteons) from blood and yeast extract. The method is based on in vitro polymerization and aggregation of proteins in plasma in sterile conditions at elevated temperatures within hours. The addition of recombinant human prion protein (RPRP) to Protein Nucleating Centers (PNC) and heating at above ambient temperatures produced extremely large quantities of intact proteons of the size 10-20 nm.

Another embodiment of this invention is a method for inducing apoptosis in cells which involves contacting cells with yeast PNC's exhibited decreased metabolic activity similar to that obtained in experiments with PNC's from shark tissues and mammalian blood.

Another embodiment involves a method of isolating and self-assembling of small protein particles. First, protein nucleating centers (PNC's) are added to a recombinant human prion protein (RPRP) biological sample. In a preferred embodiment, the biological sample will include blood or yeast. It is contemplated that other biological samples may include such human extracts as saliva, or animal biological samples as rat glioma cells or PNC's from shark tissues or mammalian blood. Next, the sample is polymerized by heating the sample to a predetermined temperature, typically between 30° C. and 100° C. In a preferred embodiment, the sample is heated to 95 degrees C. The temperature is maintained for a predetermined period of time, typically between 1 minute and 60 minutes. In a preferred embodiment, the 95 degrees C. temperature is maintained for about 15 minutes. It is contemplated that various biological samples will require varying temperatures and time periods to effectuate the polymerization. Finally, the produced prions are identified.

One example of the use of this method of isolation and self-assembling is a prion disease test for cancer and other diseases. A sample may be collected, such as saliva or blood, and PNC's are added to the sample to provoke prion production. After polymerizing the sample, the produced prions can be identified and correlated to a specific disease.

This invention has significant potential value in molecular biology and the control of prion/proteon medicated diseases in animals and man. The invention may be used in medicine, biomedical industry, pharmaceutical industry, hematology, forensic sciences, cosmetics, perfumery, and/or wine-making. Specific applications include: diagnostics of pathogenic proteons causing conformational diseases; modulators of the immune system; regulation of protein turnover; regulation of pathogenic proteons and control of conformation disease by regulating assembling and disassembling of pathogenic proteons; wound healing; blood clotting; biodetection; drug delivery; preparation of stable lubricants; improvement of stability of colloidial systems and protein solutions; differential flotation; protein purification; and preparation of gels and pastes.

BRIEF DESCRIPTION OF THE DRAWINGS

FIG. 1A is an electron micrograph prepared using transmission electron microscopy (TEM) of a type 1 proteon.

FIG. 1B is a TEM electron mircograph of another type 1 proteon.

FIG. 1C is a TEM electron micrograph of a type 2 proteon.

FIG. 1D is a TEM electron micrograph of another type 2 proteon.

FIG. 1E is a TEM electron micrograph of a negatively stained type 2 proteon.

FIG. 1F is a TEM electron micrograph of another negatively stained type 2 proteon.

FIG. 1G is an electron micrograph prepared using scanning electron microscopy (SEM) of a type 2 proteon.

FIG. 2A is a graph illustrating proteon proliferation in purified water and in blood plasma showing the number of proteons visible as a function of time.

FIG. 2B is a graph of proteon proliferation in two different growth mediums showing the number of proteons visible as a function of time.

FIG. 2C is a graph of proteon proliferation in the presence and absence of urea showing the number of proteons visible as a function of urea concentration.

FIG. 2D is a graph illustrating cyclic amplification of proteons in plasma showing the number of proteons visible as a function of the number of amplification cycles.

FIG. 3A is a TEM electron micrograph of clusters of crystalline, metallic copper nanoparticles.

FIG. 3B is a TEM electron micrograph of an amorphous matrix for the copper nanoparticles show in FIG. 3A.

FIG. 3C is an SAD pattern identifying the copper nanoparticles in FIG. 3A.

FIG. 3D is a DF image of copper nanoparticles prepared using a portion of the FCC ring of FIG. 3C.

FIG. 4A illustrates cell viability for a number of different types of cells for cultured cells incubated with PNCs for 20 hours.

FIG. 4B1 shows a dark field photomicrograph of brain glioma cells before exposure to PNCs.

FIG. 4B2 shows a dark field photomicrograph of brain glioma cells after exposure to PNCs.

FIG. 4B3 is a dark field photomicrograph of brain glioma cells after exposure to staurosporine.

FIG. 4B4 is a fluorescence photomicrograph of brain glioma cells exposed to PNCs and stained with propidium iodide.

FIG. 4C is a graph illustrating the viability of brain glioma cells obtained from various animals after exposure to PNCs at different concentrations.

FIG. 5 is a graph illustrating the proliferation of proteons over time in a tissue culture media;

FIG. 6 is a graph illustrating the number of proteons in a sample of plasma as a function of the concentration of urea in the sample;

FIG. 7 is a schematic diagram illustrating a method for destroying disease causing prions and proteons; and FIG. 8 is a schematic diagram illustrating a method of isolating and self-assembling of small protein particles.

DETAILED DESCRIPTION

The present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements.

Compositions and methods for identifying and characterizing disease states are provided. The compositions comprise misfolded proteins and misfolded proteins aggregated on a nucleation center. The aggregated proteins are referred to herein as proteons. The nucleation centers are referred to as proteon nucleation centers (PNCs).

DEFINITIONS

By "proteons" are intended protein bodies, generally on the order of a few tens of manometers up to several microns across, having misfolded or partially misfolded proteins surrounding a PNC. In one aspect of the invention, proteons can be isolated from blood, including human, bovine, horse, pig, cat, dog, fish, rabbit, and rat blood. In another aspect of the invention, proteons can be isolated from plasma, including human, bovine, horse, pig, cat, dog, fish, rabbit and rat plasma.

By "PNC" is intended the metallic nucleation centers isolated as described herein. In one aspect of the invention, PNCs can be isolated from blood, including human, bovine, horse, pig, cat, dog, fish, rabbit, and rat blood. In another aspect of the invention, PNCs can be isolated from plasma, including human, bovine, horse, pig, cat, dog, fish, rabbit, and rat plasma.

A "prion" is a PNC surrounded only by one or more misfolded proteins.

Prion diseases are neurodegenerative diseases causally linked to the partial unfolding and subsequent misfolding and aggregation of the prion protein (PrP). While most proteins fold into a single low energy state, PrP can fold into two distinct isoforms. In its innocuous state, denoted as $PrP^C$, the protein has predominately α-helical secondary structure. However, $PrP^C$ can misfold into an isoform rich in extended structure capable of forming toxic and infectious aggregates. Under certain conditions, the innocuous cellular form of the protein, $PrP^C$, can convert to the lethal scrapie prion protein isoform, $PrP^{Sc}$, which can aggregate with other PrP molecules, resist degradation and destroy neuronal and glial cells.

While PrP$^C$ is believed to play a positive role in cellular functions, PrP$^{Sc}$ is responsible for the transmissible spongiform encephalopathies (TSE), which include bovine spongiform encephalopathy in cattle, fatal familial insomnia, Creutzfeldt-Jakob disease (CJD) and Kuru in humans and the namesake of PrP$^{Sc}$, scrapie in sheep and goats. PrP$^{Sc}$, while sharing the same covalent structure as PrP$^C$, can be distinguished from PrP$^C$ based on secondary, tertiary and quaternary structure. PrP$^{Sc}$ is rich in β-structure with some α-helical structure (43-45% extended structure, 17-30% α-helix), whereas PrP$^C$ has little β-structure and is largely α-helical (3% β-structure, 47% α-helix). Unlike the monomeric PrP$^C$, PrP$^{Sc}$ can form oligmeric structures that can be cytotoxic and/or infections. PrP$^{Sc}$ does not arise from misfolding during the synthesis of PrP, but directly from PrP$^C$. For more information on the structure of the prion protein, see the discussion in DeMarco et al., "Local Environmental Effects on the Structure of the Prion Proteins," C. R. Biologies 328 (2005) 847-862, the description of which is specifically incorporated herein by reference.

By "plasma" is intended the supernatant produced by the centrifugation of blood or other suspension of biological material.

By "seeding" is intended adding an amount of either a PNC or proteon to a biological sample.

The proteons of the invention can be identified and quantified in biological samples. Such samples include serum, blood, bodily fluids such as saliva, tissue including brain, other organ tissue, and the like. To identify the proteons in tissue, the tissue is homogenized in a fluid or liquid.

Proteons can be isolated from biological samples of any mammal including but not limited to human, primate, bovine, cattle, horse, sheep, pig, cat, dog, rabbit, rat, deer, ox, mouse, and the like. They can also be detected in samples from fish, chicken, turkey, duck, and the like.

As indicated, proteons contain misfolded and/or partially misfolded proteins. In one aspect, the proteon compositions of the invention show an apple-green birefringence when stained with congo-red. This staining pattern is analogous to that obtained with prions and other amyloid proteins, all of which are included in the class of congophilic proteins. See Kelly (1996) *Curr. Opin. Struct. Biol.* 6:11-17. These proteins are associated with various disorders or disease states. Thus, the identification of proteons comprised of such proteins is indicative of a disorder or disease state. Likewise, the number of proteons in a sample comprised of such proteins is predictive of the progression of the disease. That is, the number of proteons in a sample correlates with progression of a disease state. Therefore, quantification of proteons in a sample is useful for determining or diagnosing the stage of disease or disorder and can help in planning treatments or therapies for the disease. Examples of disorders involving misfolded proteins and the relevant proteins that can be utilized in the methods of the present invention are set forth in Table 1, below. The disorders associated with congophilic proteins are set forth in Table 2, below.

It is recognized that for proper diagnosis, proteons must not only be identified, but also the misfolded protein in the proteon must be identified. Methods for protein purification and identification include antibody binding, amino acid sequencing, and the like.

Two methods for the detection of such disorders may be used. The first method involves the use of an antibody. The antibody can recognize prion-proteins and distinguish between prions that are misfolded and prion-proteins that are normal. However, the number of misfolded proteins are typically very small making detection of misfolded proteins difficult. As a result, cyclic amplification is performed to increase the number of misfolded proteins and then the antibody is used. Cyclic amplification is first performed to convert any and all partially misfolded proteins into prions. In this first method, a specific prion antibody is used that binds only to prions and not to other proteons. This is performed to distinguish between prions (misfolded prion-proteins) and normal prion proteins. These antibodies are disclosed in WO2006/046344 and WO2006/076687, the disclosures of which are both specifically incorporated herein by reference. These antibodies are commercially available from Signet Laboratories, Inc., Novus Biologicals, GeneTex, Biodesign International, Abcam and other sources. Once added to a sample containing the amplified prion proteins, the antibody binds only to the misfolded prion proteins which can then be identified by methods known to those skilled in this art.

Examples of such antibodies include the following:
Mouse Anti-Prion protein PrP Monoclonal
Antibody, Biotin Conjugated, Clone 3F4 Abcam
Mouse Anti-Prion protein PrP Monoclonal
Antibody, Horseradish Peroxidase
Conjugated, Clone 1E5/G6 Abcam
Mouse Anti-Prion protein PrP Monoclonal
Antibody, Horseradish Peroxidase
Conjugated, Clone 3B8/D5 Abcam
Mouse Anti-Prion protein PrP Monoclonal
Antibody, Horseradish Peroxidase
Conjugated, Clone 7B6/D2 Abcam
Mouse Anti-Bovine Prion Protein
Monoclonal Antibody, Unconjugated, Clone
WD3C7
BIODESIGN International
Mouse Anti-Prion Protein (PrP) Monoclonal
Antibody, Unconjugated, Clone BDI115
BIODESIGN International
Mouse Anti-Prion PrP (109-112)
Monoclonal Antibody, Biotin Conjugated,
Clone 3F4
BIODESIGN International
Mouse Anti-Bovine Prion Protein (PrP)
Monoclonal Antibody, Unconjugated, Clone
F89/160.1.5
Calbiochem
Mouse Anti-Prion Monoclonal
Antibody, Unconjugated, Clone F89/160.1.5
Calbiochem
Anti-Prion Monoclonal Antibody, Biotin
Conjugated, Clone 1E4
Cell Sciences
Anti-Prion Monoclonal Antibody,
Horseradish Peroxidase Conjugated, Clone
1E4
Cell Sciences
Anti-Prion Protein (PrP) Monoclonal
Antibody, Unconjugated Clone 3F4
CHEMICON
Mouse Anti-Prion protein PrP Monoclonal
Antibody, Biotin Conjugated, Clone 3F4
GeneTex
Mouse Anti-Prion protein PrP Monoclonal
Antibody, Horseradish Peroxidase
Conjugated, Clone 1E5/G6
GeneTex
Mouse Anti-Prion protein PrP Monoclonal
Antibody, Horseradish Peroxidase
Conjugated, Clone 3B8/D5
GeneTex Mouse Anti-Prion protein PrP Monoclonal Antibody, Horseradish Peroxidase Conjugated. Clone 7B6/D2
GeneTex
Mouse Anti-Prion protein (PrP) Monoclonal Antibody, Horseradish Peroxidase Conjugated, Clone 1E5/G8
Novus Biologicals
Mouse Anti-Prion protein (PrP) Monoclonal Antibody, Horseradish Peroxidase Conjugated, Clone 3B8/D5
Novus Biologicals
Mouse Anti-Prion protein (PrP) Monoclonal Antibody, Horseradish Peroxidase Conjugated, Clone 7B6/D2
Novus Biologicals
Mouse Anti-Prion protein (PrP) Monoclonal Antibody, Unconjugated. Clone 1E5/G6
Novus Biologicals
Mouse Anti-Prion protein (PrP) Monoclonal Antibody, Unconjugated. Clone 3B8/D5
Novus Biologicals
Mouse Anti-Prion protein (PrP) Monoclonal Antibody, Unconjugated. Clone 7B6/D2
Novus Biologicals
Mouse Anti-Prion protein (PrP) Monoclonal Antibody, Unconjugated. Clone F89/160.1.5
Novus Biologicals
Mouse Anti-Prion protein (PrP) Monoclonal Antibody, Unconjugated, Clone 3F4
Novus Biologicals
Rabbit Anti-Prion Protein Antibody
Unconjugated
Novus Biologicals
Anti-Human Prion Protein Monoclonal Antibody, Biotin Conjugated, Clone 3F4
Signet Laboratories, Inc.
Anti-Human Prion Protein Monoclonal Antibody, Biotin Conjugated, Clone 3F4
Signet Laboratories, Inc.
Anti-Human Prion Protein Monoclonal Antibody, Biotin Conjugated, Clone 3F4
Signet Laboratories, Inc.

In the second method, prions are also being detected, and, again, cyclic amplification is first performed to convert all partially misfolded prions into prions (which are misfolded prion-proteins aggregated around PNC). Next a digestive enzyme such as Proteinase K is added to digest the normal prion-proteins. It can also digest partially misfolded prion-proteins, if there are any left, but this isn't likely because of the cyclic amplification step. Third, a prion antibody is added which is not specific in that it cannot distinguish between normal prion-proteins, partially misfolded prion-proteins and misfolded prion-proteins. However, the antibody will find and bind only to prions (misfolded prion-proteins) because the digestive enzymes destroyed the normal prion-proteins and the cyclic amplification step converted all partially misfolded prions into prions. This second method, therefore, includes the following: 1. cyclic amplification; 2. add digestive enzymes and 3. add non-specific antibody. The remaining steps of identifying the protein and correlating to a disease are then the same as in the first method.

Proteinase K is available commercially from Sigma-Aldrich Chemicals Inc.

TABLE 1

Conformational diseases. See Carrel and Lomas (1997) *Lancet* 350: 134138; Carrell and Gooptu (1998) (1998) *Cure Op. Struc. Biol.* 8: 799-809.; Soto (2001) *FEBSLetters* 498: 204-207; Jaikaran and Clark (2001); Ursini et al. (2002) *Trends Mol. Med.* 8: 370-374; Kannan et at. (1988) *J. Biol. Chem.* 263: 13766-13773; Schluter and Drenckhahn (1986) PNAS 83: 6137-6141; Gerner et al. (2002); Davis et al. (2002)*Lancet* 359: 2242-2247; Fernandez et al. (2001) *Atherosclerosis* 158, 103-111 (atherosclerosis); Papalexis et al. (2001) *Mol. Biochem. Parasitology* 115: 77-86; Esievo et al. (1984) *Veterinary Parasitology* 15: 181-185; Igoe et al. (2002) *Clin. Microb. Newsletter* 24: 6970; Kreidl et al. (2002) *J. Am. Coll. Surgeons* 194: 387; Beckers (2001) *Netherlands J.. Med* 58: 204-207 (autoimmune diseases); Ismeno et al. (1999) *Int'l J. Cardiology* 69: 179-183; Klibansky et al. (1966) Toxicon 3: 213-216; Seibert et al. (2003) *Toxicon* 41: 831839; Szabo et al. (2002) *Thrombosis Research* 107: 357-363; Kaioumova et al. (2001) *Chemosphere* 43: 801-805.

| Protein | Disease |
|---|---|
| Hemoglobin | Sickle cell anemia and aggregates |
| | Heinz bodies in aged erythrocytes |
| | Unstable hemoglobin inclusion body hemolysis |
| | Drug induced inclusion body hemolysis |
| | Aggregates regulate apoptosis in cancer patients |
| | Atherosclerosis |
| | Malaria |
| | Tnfections |
| | Auto-immune disorders |
| | Toxic reactions |
| | Internal bleedings |
| Prion protein | Creutzfeld-Jacob disease (CJD) |
| | New variant CJD |
| | Bovine spongiform encephalopathy (BSE) |
| | Gerstmann-Straussler-Schheinker disease |
| | Fatal familial insomnia |
| | Kuru |
| β-amyloid | Alzheimer's disease |
| | Down's syndrome |
| | Familial Alzheimer's |
| α-Synuclein | Parkinson's disease, Lewy bodies |
| Tau protein | Frontotemporal dementia, Pick bodies |
| Serpins | $\alpha_1$-antitrypsin deficiency |
| | cirrhosis |
| | emphysema |
| | Antithrombin deficiency |
| | thrombosis |
| | $C_1$-inhibitor deficiency |
| | angioedema |
| Neuroserpin | Neurodegenerative disease, Collins bodies |
| Glutamate repeats | Inherited neurodegenerative disorders |
| | Huntington's disease |
| Amylin | Diabetes type II |
| SOD | Amyotrophic lateral sclerosis |
| ApoB | Atherosclerosis |
| CFTR protein | Cystic fibrosis |
| Immunoglobulin | Systemic amyloid light chain amyloidosis |
| Amyloid light chain | Nodular amyloidosis |
| Serum amyloid A | Reactive systemic amyloid A amyloidoses |
| | Chronic inflammatory disease |
| Transthyretin | Senile systemic amyloidosis |
| | Familial amyloid neuropathy |
| | Familial cardiac amyloid |
| $B_2$-microglobulin | Hemodialysis amyloidosis |
| | Prostatic amyloid |
| Apolipoprotein AI | Familial amyloid polyneuropathy |
| | Familial visceral amyloid |
| Cystatin C | Hereditary (Icelandic) cerebral angiopathy |
| Lysozyme | Familial visceral amyloidosis |

TABLE 2

Congophilic disorders. See Kelly (1996) *Curr. Opin. Struct. Biol.* 6: 11-17.

| Disorder Acronym | Disorder | Protein Involved |
|---|---|---|
| CJD | Spongiform enc alo athies | Prion protein fragments |
| APP | Alzheimer | Beta protein fragment 1-40/43 |
| HRA | Hemodialysis-Related Amyloidosis | Beta-2 microglobin* |
| PSA | Primary Systematic Amyloidosis | Immunoglobin light chain and fragments |
| SAA 1 | Second Systematic Amyloidosis | Serum amloid A 78 residue rragment |
| FAP I** | Familial Amyloid Polyneuropathy I | Transthyretin fragments, 50+ alleles |
| FAP III | Familial Amyloid Polyneouropathy III | Apolipoprotein A-1 fragments |
| CAA | Cerebral Amyloid Angiopathy | Cystatin A minus 10 residues |
| FHSA | Finnish Hereditary Systemic Amyloidosis | Gelsolin 71 residue |
| LAPP | Type II Diabetes | Islet amyloid polypeptide fragment |
| ILA | Injection-Localized Amyloidosis | Tnsulin |
| CAL | Medullary Thyroid Carcinoma | Calcitonin fragments |
| ANF | Atrial Amyloidosis | Atrial natriuretic factor |
| NNSA | Non-Neuropathic Systemic Amylodosis | Lysozyme and fragments |
| HRA | Hereditary Renal Amyloidosis | Fibrinogen fragments |

*Homologous to immunoglobin, thus a predicted paralogous disease.
**Also called senile systemic amyloidosis, prealbumin is synonymous with transthyretin. See mad-cow.org/congo.html (the prefix "www" is required).

Immunohistochemical assays have been developed for the proteins listed in Tables 1 and 2. See, e.g., Hardt et al. (2000) *J Camp. Path.* 122:43-53 (antibodies for the detection of the prion protein, PrP). However, many of these proteins are only abundant in the late stages of the disease and may be undetectable utilizing standard assay techniques. Thus, in one embodiment, the methods of the present invention may be combined with an immunochemical assay for the protein or proteins selected from Tables 1 and 2. These proteins, or their functional derivatives, may be detectably labeled with any appropriate marker such as a radioisotope, an enzyme, a fluorescent label, a paramagnetic label, or a free radical linked to an antibody capable of binding these proteins.

Methods of making and detecting such detectably labeled antibodies or their functional derivatives are well known to those of ordinary skill in the art, and are described in more detail below. See, for example, Klein (1982) *immunology: The Science of Self-Nonself Discrimination* (John Wiley & Sons, New York 1982); Kennett et al. (1980) *Monoclonal Antibodies and Hybt idomas: A New Dimension in Biological Analyses*, (Plenum Press, New York; Campbell (1984) *Monoclonal Antibody Technology, Laboratory Techniques in Biochemistry and Molecular Biology*, Volume 13, ed. Burdon et al. (Elsevier, Amsterdam; and Eisen (1980) in *Microbiology*, ed. Davis et al. 3d ed.; Harper & Row, Philadelphia. Methods for the generation of polyclonal antibodies are known, as are techniques for the generation of monoclonal antibodies See, e.g., Kohler and Milstein (1975) *Nature* 256:495-497.

Assay techniques useful in the present invention include, but are not limited to, assays comprising incubating a biological sample from a subject suspected of having such a condition in the presence of a detectably labeled binding molecule (e.g., antibody) capable of identifying the relevant protein, and detecting the binding molecule which is bound in a sample. See, e.g., Work et al. (1978) *Laboratory Techniques and Biochemistry in Molecular Biology* (North Holland Publishing Company, NY.

Alternatively, the proteins contained in a particular sample of proteons can be identified by screening against a panel of phage antibodies in which the displayed peptide is a domain of the antibody molecule that includes the site that binds antigen. Phage-antibody libraries can be constructed including billions of clones, displaying billions of antibodies with different antigen specificities. For a review of this technique, see Petrenko and Vodyanoy (2003) *J Micro. Meth.* 53:253-262.

The presence of proteons themselves can be detected and quantitated by dark-field microscopy. Under high-resolution dark-field microscopy proteons are visualized as bright spherical shapes. Techniques for dark-field microscopy are known in the art. See, e.g., Bradbury and Bracegirdle (1998), *Introduction to Light Microscopy* (*Microscopy Handbooks*, No 42), 2d ed.; (Springer Verlag). In particular, proteons are small, ball-like bodies of different sizes, estimated in the range of 50-250 nm. By contrast, healthy erythrocytes appear as bright void circles of about 7 microns diameter in the dark-field view, whereas neutrophils are roughly 7-15 microns. When a blood sample becomes aged, the morphology and number of the proteons change, with some estimated to be 500 nm in diameter. Some appear attached to the internal surface of the erythrocyte membrane. Proteons are found in fresh blood of species including human, bovine, horse, pig, cat, dog, fish, rabbit, and rat blood.

Dark-field microscopy of proteons can be confirmed by transmission electron microscopy (TEM) and scanning electron microscopy (SEM) methodology. Techniques for electron microscopy are known in the art. See, e.g., Slayter and Slayter (1992) *Light and Electron Microscopy*, (Cambridge University Press).

Proteons can be isolated from blood or plasma, i.e., the supernatant produced by centrifuging a biological material. In one embodiment, proteons can be formed by incubating plasma at 37° C. under sterile conditions over a thirteen day period. At the end of this period, the numbers of proteons observed under dark-field light microscopy are greatly increased.

In another embodiment, large numbers of proteons are produced by subjecting plasma to 120° C. at 20 psi for two hours. The visible number of proteons is amplified by subjecting plasma to a single step of elevated temperature.

Efficiency of proteon production is enhanced by taking a small portion of an amplified sample, adding it to an untreated sample, and heating the untreated sample. These steps can be repeated a number of times, each iteration yielding an increased quantity of proteons. Accordingly, by dividing the sample into a number of subsamples, subjecting the first subsample to heat or pressure, then aliquoting a small amount of the proteons from the first subsample into the second subsample and carrying out the heating step, a greater concentration of proteons can be produced from the second subsample than was produced from the first subsample. These seeding steps can be repeated multiple times until, after several iterations, the concentration of proteons produced per volume of sample eventually plateaus.

Typically, the first two cycles result in a small but significant increase of proteon population, whereas the third cycle brings about a dramatic increase in the number of proteons. Generally, the next three cycles resulting saturation of the protean population.

In one embodiment, a test sample containing a small amount of misfolded proteins is subjected to a single heating step. The amplified proteons are quantitated by dark-field microscopy and verified by immunfluorescent techniques to detect the misfolded protein.

In another embodiment, a small amount of seeds such as the PNCs described above can be added to a test sample to increase the sensitivity of the single step methods. Roughly $5\times10^{13}$ PNC/ml are produced by initial filtration of plasma through a 5 kD filter. This concentration then can be increased by a factor of roughly 100 by evaporation. Thus, in one aspect, addition of 5 ml of $5\times10^{13}$ PNC/ml to a 1 ml sample increases the concentration of $PNC^-$ in a sample by 2 $5\times10^{11}$ PNC/ml. This concentration is increased by a factor of 100 if pre-concentrated PNC are added. If the initial concentration of PNC varies from $10^8$ to $10^{11}$ PNC/ml, the sensitivity can be increased by a factor of between 250 to 250,000.

In another embodiment, the first step amplification described above is carried out, then a small portion of amplified sample is introduced into the untreated sample and subjected to heat again. Then, the small portion of the second amplified sample is added to the third untreated sample, heated, and so on. The number of cycles depends on the initial concentration of misfolded proteins. Suitable numbers of cycles include 1, 2, 3, 4, 5, 6, 7, 8, 9, 10, 15, 20, 25 or more.

In one embodiment, the detection and identification can be done as a single-step method. Apparatus for subjecting a sample to heat and/or pressure are recognized in the art and include without limitation, PCR thermocyclers, autoclaves, etc.

As will be recognized by one of skill in the art, both the single- and multiple-step methods can be manipulated by varying the temperature, pressure, or temporal parameters. Suitable temperatures include 37, 40, 45, 50, 55, 60, 65, 70, 75, 80, 85, 90, 95, 100, 105, 110, 115, or 120° C. Suitable pressures include ambient pressure, as well as 14, 15, 16, 17, 18, 19, 20, 21, 22, 23, 24, or 25 psi. Suitable times of treatment include 1, 5, 10, 15, 20, 25, 30, 35, 40, 45, 50, 55, 60, 65, 70, 75, 80, 85, 90, 95, 100, 105, 110, 115, and 120 minutes.

In another embodiment, these methods can be utilized to clear misfolded proteins from a biological sample such as blood. Because low temperatures can be utilized with long time periods, this can be accomplished without damaging the biological sample.

In another embodiment, these methods can detect misfolded proteins involved in congophilic disorders. See Kelly (1996) *Curt-. Op. Struc. Biol.* 6:11-17; Kelly (1996) 8:101-106. For instance, there is a demonstrated structural homology between prion and hemoglobin proteins. Korth et al. (1997) *Nature* 390:74-77. There is evidence that prions are present in lymphoid organs and blood. See, e.g., Brown et al. (2001) *J Lab. Clin. Med.* 137:5-13; Aguzzi (2000) *Lab. Clin. Med.* 137:5-13; Aguzzi (2001) *Nature Medicine* 7:289-290; Wadsworth et al. (2001) *Lancet* 358:171-180. Accordingly, the methods of the present invention can be utilized for amplification of a congophilic protein, thus allowing early detection of disorders related to these proteins.

PNC of roughly 1-2 nm—and containing about 40-300 atoms play an important role in capturing hemoglobin released into blood plasma. While released hemoglobin is normally captured by protein haptoglobin and endocytosed by macrophages; released hemoglobin can be collected by PNCs. Roughly $7\times10^{13}$ PNC are present in each milliliter of human blood, while only 0.003% of the whole pool of PNC is normally linked to proteins and made into proteons. However, a proteon of medium size of 160 nm can collect about 100,000 protein molecules of similar size to hemoglobin. Thus, the strong protein scavenging properties of metal nanoparticles allow them to collect proteins including misfolded hemoglobin (Kristiansen et al. (2001) *Nature* 409:198).

Thus, in another embodiment, the present methods can be utilized for amplification of proteins involved in intravascular hemolysis and resulting in aggregation of hemoglobin, including, without limitation, sickle cell anemia, atherosclerosis, malaria, infections and their complications, auto-immune disorders, internal bleedings and intravascular hemolysis due to internal prosthetic devices, and toxic reactions. See Kannan et al. (1988) . . . *Biol. Chem.* 263:13766-13773; Schluter and Drenckhahn (1986) *PNAS* 83:6137-6141 (sickle cell); Fernandez et al. (2001) *Atherosclerosis* 158$_{,1}$103111 (atherosclerosis); Papalexis et al. (2001) *Mol. Biochem. Parasitology* 115:77-86, Esievo et al. (1984) *Veterinary Parasitology* 15:181-185; Igoe et al. (2002) *Clin. Microb. Newsletter* 24:69-70; Kreidl et al. (2002) *J. Am. Coll. Surgeons* 194:387; Beckers (2001) *Netherlands J. Med:* 58:204-207 (autoimmune diseases); Ismeno et al. (1999) *Int'l J. Cardiology* 69:179-183; Klibansky et al. (1966) *Toxicon* 3:213-216, Seibert et al. (2003) *Toxicon* 41:831-839; Szabo et al. (2002) *Thrombosis Research* 107:357-363; Kaioumova et al. (2001) *Chemosphere* 43:801-805.

Using standard techniques, samples for single-step or cyclic amplification can be prepared from homogenates of small tissue fragments, or from biological fluids such as blood, cerebrospinal, lymph, etc. Techniques for the preparation of tissue homogenates and biological fluids from such sources are known. See Sambrook et al. (1989) *Molecular Cloning—A Laboratory Manual, Vols.* 1-3 (2d ed; Cold Spring Harbour Laboratory Press, Plainview, N.Y.); and Ausubel et al., eds. (1994) *Current Protocols in Molecular Biology*, (Greene Publishing Associates, Inc. and John Wiley & Sons, Inc.).

PNCs can be produced from plasma by filtration through an ultrafiltration membrane. In one embodiment, plasma is filtered consecutively through a 30 kD and a 5 kD CENTRICON™ filter from Millipore Corp. before heat treatment. The centrifuge filtration is carried out using an initial' volume of 80 ml centrifuged at 3,500 g for 20 minutes, 20° C.

Filtration of plasma before heat treatment abolishes proteon formation in the retentate. However, recombination of the fractions results in the resumption of proteon formation, and the number of proteons formed is dependent upon the amount of filtrate added back to the retentate. Thus, the PNCs are present in the filtrate.

Adsorption spectra of the filtrate reveals the presence of metals, including copper, zinc, and iron, indicating that PNCs comprise metals. The filtrate was precipitated with 1.2 mM $MgSO_4$ and TEM studies were carried out. Such procedures are known in the art. See, e.g., Shindo and Oikawa, *Analytical Electron Microscopy for Materials Science*, Springer-Verlag (2002). It was found that the precipitated extract contained crystalline metallic nanoparticles of roughly 1-2 nm diameter. Selected area diffraction patterns were consistent with the presence of face centered cubic (FCC) or body centered cubic (BCC) metals or solid-solution alloys such as FCC copper and BCC iron.

For a review of metal clusters, see Aiken and Finke (1998) *J Mol. Cat. A: Chem.* 145:1-44; Gonzalez-Moraga (1993) *Cluster Chemistry* (Springer-Verlag, New York, N.Y.). High symmetry is one of the main characteristics of metal clusters (Gonzalez-Moraga (1993) (Supra). In addition, metal clusters bind proteins. See Broun et al, (2002) *J Mol. Biol.* 321:341-353; Liu and Xu (2002) *J Inorganic Biochem.* 88:77-86. Thus, in-one embodiment, the PNCs of the invention are characterized by small size, a few nm, or smaller. Additionally, the PNCs are present in large quantities, about $10^{12}$-$10^{13}$ PNC/cm$^3$ of blood or tissue, are abundant, present binding sites and strong affinity to proteins, exhibit variability to bind different proteins, and resist extreme physical and biochemical conditions.

To test the effects of PNCs isolated from the filtrate upon living cells, various amounts of PNCs obtained by ultrafiltration and sterilized by autoclaving were incubated for four hours with various animal cells in tissue culture. Significant effects upon cell viability were observed. For instance, rat and mouse glioma cells demonstrated marked signs of cell death, as assessed both microscopically and by MTT assay. Accordingly, the PNCs of the invention comprise a novel reagent for use in inducing apoptosis, as well as a process for its production. In one embodiment, aliquots from 1 to 40 µl containing about $1 \times 10^{12}$ to $4 \times 10^{13}$ PNCs were added to 100 gl wells of 96-well ELISA plate. Such compounds- and processes are of great usefulness to those of skill in-the-art. See, e.g., U.S. Pat. No. 5,344,926 to Murakata et al., titled "Process for producing staurosporine derivatives"; U.S. Pat. No. 4,973,552 to Schroeder et al., titled "Staurosporine fermentation process"; and U.S. Pat. No. 6,518,032 to Fritz et al., titled "Rapid methods for identifying modifiers of cellular apoptosis activity."

Figure 5:
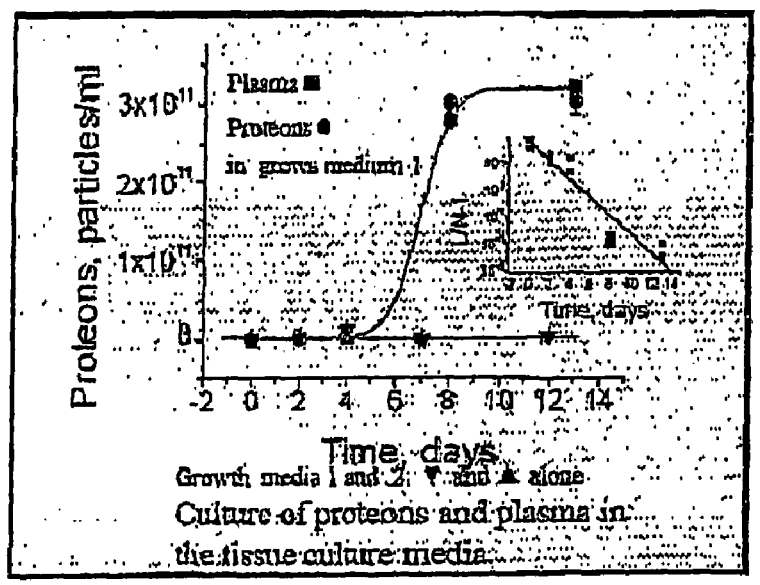

The schematic representation of FIG. 5 depicts a proteon, which is a Protein Nucleation Center (PNC) surrounded by misfolded and/or partially misfolded proteins, which are wrapped around the PNC. Proteons are naturally occurring particles in the blood, and are present at a concentration of approximately $10^8$ proteons per milliliter of blood.

Figure 6:
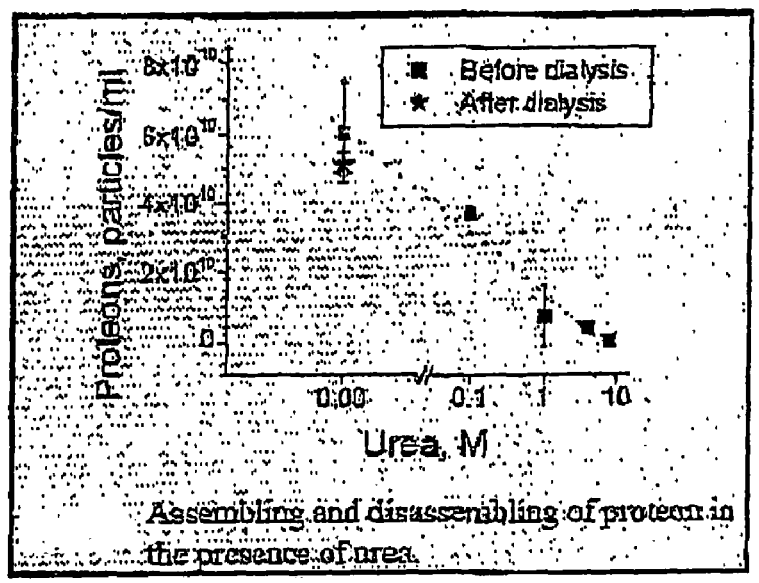

FIG. 6 depicts a schematic representation of a prion. A prion is a PNC surrounded by only misfolded proteins. Therefore, all prions are proteons, but not all proteons are prions. It should also be noted that PNCs are a metal particle, such as iron or copper, having a size of approximately 10-20 angstroms. PNCs occur in the blood at an approximate concentration of $10^{13}$ PNC per milliliter of blood.

Figure 7:
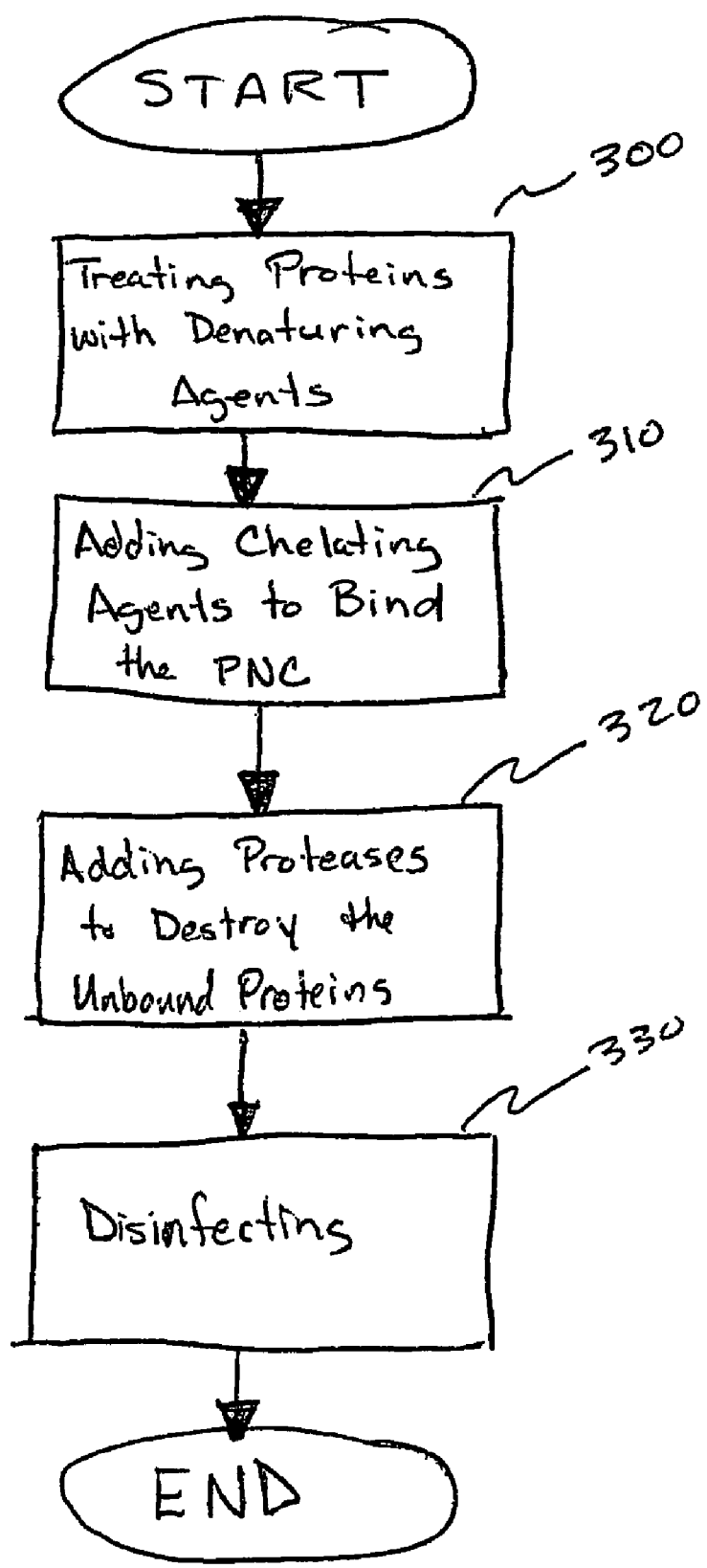

FIG. 7 illustrates the method utilized to destroy disease causing prions and proteons. In step 300, the prions and proteons are treated with denaturing agents, which cause the proteins to unfold from the prion or proteon to render the metal PNC component of the prion or proteon subject to chelation by suitable ligands. The denaturing agent may include, but is not limited to, urea, guanidinium salts, trimethylamine N-oxide, and other certain sugars. After the denaturing agent are used to unfold the proteins in step 300, chelating agents are added to the exposed PNC in step 310. The chelating agents used include, but are not limited to, the class of aminopolycarboxylates such as EDTA, EDPA, NTA and others known in the art. These chelating agents effectively immobilize the PNCs, thus neutralizing the deleterious properties of the prions or proteons. In step 320, proteases enzymes are added to the PNC and related proteins in order to destroy the proteins by digesting these non-bound proteins. In step 330, the remaining proteins and PNCs are disinfected by adding a disinfecting agent, preferably by adding creosote. Other disinfectants may also be used in step 330 in some applications such as chlorine, bromine or other biocides.

Figure 8:
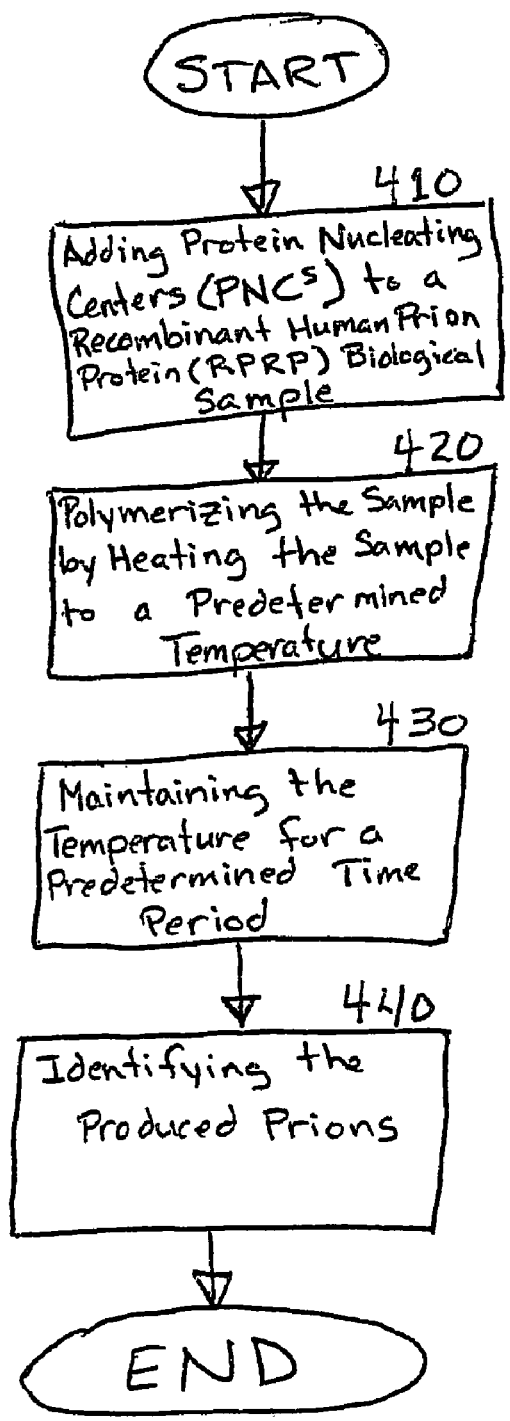

FIG. 8 illustrates the method of isolating and self-assembling of small protein particles. In step 410, protein nucleating centers (PNC's) are added to a recombinant human prion protein (RPRP) biological sample. In a preferred embodiment, the biological sample will include blood or yeast. It is contemplated that other biological samples may include such human extracts such as saliva, or animal biological samples such as rat glioma cells or PNC's from shark tissues or mammalian blood. In step 420, the sample is polymerized by heating the sample to a predetermined temperature, typically between 30° C. and 100° C. In a preferred embodiment, the sample is heated up to about 95 degrees C. In step 430, the temperature is maintained for a predetermined period of time, typically between 1 minute and 60 minutes. In a preferred embodiment, the 95 degrees C. temperature is maintained for 15 minutes. It is contemplated that various biological samples will require varying temperatures and time periods to effectuate the polymerization. In step 440, the produced prions are identified.

This invention is further illustrated by the following examples that should not be construed as limiting

EXPERIMENTAL

EXAMPLE 1

Production of Proteons from Blood and Analysis by Microscopy

A 30 µl sample of freshly drawn full blood from a healthy human male was obtained and diluted in 1000 µl of purified water in a 1.5-ml plastic vial, and centrifuged at 2200 g (6000 rpm) to obtain plasma. An additional aliquot of the blood was taken and prepared for optical dark-field microscopy. The plasma was transferred to a 4-ml glass vial with a plastic cap and a teflon liner. An aliquot of plasma was again retained for dark-field microscopy. The vial and contents were subjected to heating at a temperature of 120° C. and 20 psi of pressure for two hours. An aliquot of the heat-treated plasma was prepared for dark-field microscopy.

Each aliquot retained for microscopy was analyzed by dark-field microscopy using an OLYMPUS™ microscope fitted with a 100W mercury lamp, a polarizer, and a Naessens dark-field condenser (COSE Corp., Canada).

After analysis, the fresh full blood sample was found to contain approximately $3 \times 10^8$ proteons/ml, whereas the diluted sample contained roughly $9 \times 10^6$ proteons/ml. The treated sample contained an estimated $3 \times 10^{11}$ proteons/ml, a five-order of magnitude increase. Adjusted for the initial dilution of the blood sample, each milliliter of blood yielded roughly $1 \times 10^{13}$ proteons. Thus, within two hours, the number of proteons increased by approximately 5 orders of magnitude. Assuming exponential growth, then the number of proteons (N) at any given moment of time (t) can be described by the equation:

$$N = N_0 e^{bt}$$

where $N_0$ is the initial number of particles, and b is the growth coefficient. If N, $N_0$, and t are substituted with the experimental values found in the above experiment, one can estimate that the growth coefficient (b) for this case is equal to 5.2 1/hour, and the proteon population is doubled every 8 minutes.

As a control, a suspension of phospholipids and cholesterol was subjected to the same protocol used for the blood sample. However, no structures resembling proteons were observed under dark-field microscopy.

Electron microscopy analysis was also carried out on samples obtained before and after heat treatment. Transmission electron microscope (TEM) images obtained from pre- and post-heat-treatment samples reveal small proteons appearing as dark discs with a rough and fibrous appearance. An analysis of the TEM images revealed the size distribution of this characteristic small protean to reach a maximum about 150 nm.

Another characteristic form of proteon was observed, a coconut-shaped particle of about 1-5 microns with a structure resembling one or more nuclei and a cell-like appearance. The nuclei look very similar to the small proteons described above. A cross-sectional view of a larger proteon reveals a very distinctive external membrane-like structure. This membrane-like structure, however, looks very different from the bacterial wall or the mammalian cell membrane, appearing as a curly fibrous shell of 10-12 ran thick. Some fiber-like structures and a few nuclei are visible inside the proteon. Images obtained by scanning electron microscopy (SEM) confirm the presence of both small and large characteristic proteons.

EXAMPLE 2

Chemical Composition of Proteons

Energy Dispersive Spectroscopy Analysis

The chemical composition was determined by energy dispersive X-ray spectroscopy using a JSM-840™ SEM system (JEOL Ltd.) using standard procedures for identifying and quantifying elemental composition. Such procedures are known in the art. See, e.g., Shindo and Oikawa (2002) *Analytical Electron Microscopy for Materials Science* (Springer-Verlag).

A sample of proteons suspended in distilled water was deposited on the aluminum SEM mount and dried in a vacuum for 24 hours. The X-ray spectra were obtained with an electron beam size of 200 run at 80 kV for 90 s. Spectra revealed that the proteons were composed of carbon, oxygen, nitrogen, and sulfur, and the presence of potassium, sodium, chloride, silicon, and copper was also detected. The presence of carbon, nitrogen, and sulfur was confirmed by analytical chemical analysis (Leco Corporation, Michigan, USA). Notably phosphorus, a necessary element of DNA, was never detected in the proteon samples. On the other hand, all the elements needed for amino acids and protein-, are available.

Amino Acid Composition

Free amino acid composition of samples before and after heat and high pressure treatment were determined (LPSA, University of Arizona, Tucson, Ariz.). See Table 3.

TABLE 3

Amino acid composition (pmol/50 ul)

| No | Amino acid | Control* | Proteons |
|---|---|---|---|
| 1 | O-Phosphoserine | 98.731 | 39.878 |
| 2 | Taurine | 191.790 | 227.739 |
| 3 | O Phosphoethanolamine | 17.980 | 15.318 |
| 4 | Urea | 220.811 | 62.573 |
| 5 | Aspartic Acid | 137.212 | 123.086 |
| 6 | Threonine | 365.225 | 214.981 |
| 7 | Serine | 385.160 | 314.039 |
| 8 | Asparagine | — | 95.908 |
| 9 | Glutamic Acid | 483.645 | 229.149 |
| 10 | Glutamine | 287.073 | 3.920 |
| 11 | Glycine | 985.419 | 922.430 |
| 12 | Alanine | 443.165 | 448.792 |
| 13 | Citralline | 81.803 | — |
| 14 | Valine | 188.720 | 236.126 |
| 15 | Cystine | 4.799 | 6.367 |
| 16 | Methionine | — | 77.583 |
| 17 | L-Cystathio-nine | 12.301 | 16.417 |
| 18 | Isoleucine | 82.836 | 76.302 |
| 19 | Leucine | 121.941 | 139.060 |
| 20 | Tyrosine | 68.636 | 75.682 |
| 21 | Phenylalanine | 104.921 | 79.904 |
| 22 | γ-Amino-butiric Acid | — | 108.022 |
| 23 | Etanolamine | 36.578 | 35.605 |

TABLE 3-continued

Amino acid composition (pmol/50 ul)

| No | Amino acid | Control* | Proteons |
|---|---|---|---|
| 24 | L-Ornithine | 53.341 | 23.004 |
| 25 | Lysine | 226.033 | 208.597 |
| 26 | Histidine | 75.954 | 103.043 |
| 27 | Arginine | 273.221 | 166.512 |

*Pre-heat and high-pressure treatment plasma.

Protein Concentration

The quantitative analysis of proteins the proteon samples was carried out by two different protein assays obtained from Bio-Rad Laboratories and Sigma-Alrich Chemical Company according to the manufacturers' protocols. Samples of blood as described in the Example 1 were exposed to different temperatures and pressures. Results of the experiments are shown in Table 4.

TABLE 4

Protein concentrations in proteon samples.

| Sample, Condition | BIO-RAD, Protein concentration, μg/ml | SIGMA, Protein concentration, μg/ml |
|---|---|---|
| Plasma, control, 25° C. | 0.67 ± 0.05 | 0.85 ± 0.2 |
| Plasma, 56° C., normal pressure, 10 min | 0.72 ± 0.04 | 0.98 ± 0.2 |
| Plasma, 80° C., normal pressure, 10 min | 0.68 ± 0.04 | 1.0 ± 0.2 |
| Proteons, 120° C., 20 psi, 2 hours | 0.71 ± 0.04 | 1.7 ± 0.2 |

Gel electrophoresis of plasma and two major protein components of plasma, albumin and hemoglobin, treated with 120° C. heat and 20 psi pressure produce obvious bands of 66,200 D and 14,400 D. These are shared with albumin and hemoglobin, respectively. After the treatment, the albumin has two weak bands of 14,400 D and ~8,000 D, which coincide with the same bands of proteons. The treated hemoglobin conserved only the 8,000 D band. Proteons filtered through a 100 kD filter conserved the 14,400 and ~8,000 bands, while proteons washed from the filter contain practically all bands of plain proteons, indicating that misfolded albumin and hemoglobin may be present in proteons. The confirmation of this fact may be obtained from the immunoblotting analysis.

Proteons from rabbit blood were disassembled by sodium dodecyl sulfate (SDS), a negatively charged detergent. The fragments of proteins were electrophoresed down and made distinctive bands in the polyacrylamide gel. The proteins were identified by N-terminal amino acid sequencing, yielding the partial sequence VLSPA (SEQ ID NO:1) (D/E)(E/K)TN(A/I) that shows 100% homology with the rabbit alpha chain of hemoglobin. Amino acide analysis showed that proteons are enriched by hydrophilic negatively charged amino acids, glutamic and aspartic acids. Proteons stained with congo-red show an apple-green birefringence with polarizing light indicating the anisotropic alignment of the dye molecules.

Congo-red staining is indicative of a common structural feature shared by many amyloids. Specifically, they are stabilized in part by anti-parallel beta sheet extensions from one monomer to another. It is believed that the dye binds to inter-monomer clefts between anti-parallel beta edge strands. See Kelly (1996) *Curr. Op. Struc. Biol.* 6:11-17; Kelly (1996) *Curr. Op. Struc. Biol.* 8:101-106. One protein belonging to the congophilic family is the prion protein associated with the prion diseases. A structural homology between prion and hemoglobin proteins has been demonstrated (Korth et al. (1997) Nature 390:74-77). In particular, two prion PrP(1121-231) molecules could be superimposed with two β subunits of the crystal lattice of sickle cell hemoglobinlHBS. The superposition included the backbone atoms of residues 145-154, 179-189, and 201-217 of the helices 1, 2, and 3 of PrP(121 231) and of residues 514, 106-116, and 125-141 of the helices 1, 6, and 7 of hemoglobin S.

Absence of DNA in Proteons

An aliquot of blood pre- and post-treatment (see Example 1) was purified using the DNEASY™ genomic DNA isolation tissue kit (Qiagen Corp.) according to the manufacturer's standard protocols for animal blood and bacteria. After final elution, samples were loaded on 1% agarose gel. DNA bands were visualized with ethidium bromide. DNA was detected in pre-treatment sample and undetected in the post-treatment sample.

Similar results were obtained using a HIGH PURE™ PCR template preparation kit (Roche Corp.) for isolation of nucleic acids followed by fluorometric quantitation of double-stranded DNA using the PICO GREEN™ dsDNA quantitation reagent (Molecular Probes Inc.) and TEACAN SPECTRAFLUOR PLUS™ fluorescence and absorbance reader equipped with DELTASOFT™ software for detecting fluorescence (excitation at 485 nm and emission at 535 nm). See Table 4.

TABLE 5

Fluorometric quantitation of DNA in blood and proteons.

| Sample | DNA concentration, µg/ml |
|---|---|
| Blood | 45.1 |
| Blood after dilution and centrifugation | 3.0 |
| Proteons, freshly prepared | 0.033 |
| Proteons, 3 months old | <0.001 |

EXAMPLE 3

Controlled Growth of Proteons

Two identical sets of samples were prepared for this experiment, in which the growth of proteons incubated at –37° C. in an atmosphere of ambient air was compared with the growth of proteons incubated in an atmosphere of 5% $CO_2$. Each set included the following numbered groups:

Group 1. Three ml of freshly prepared proteons (as described in Example 1).
Group 2. Three ml of plasma after dilution and centrifugation (as described in Example 1).
Group 3. Ten µl of freshly prepared proteons added to 3 ml of D6429 tissue culture media (Sigma Inc.) with 10% FBS (HyClone Labs. Inc.).
Group 4. Ten µl of freshly prepared proteons added to 3 ml of D5648 tissue culture media (Sigma Inc.) with 10% FBS (HyClone Labs. Inc.).
Group 5. Ten µl of freshly prepared plasma added to 3 ml of D6429 tissue culture media (Sigma Inc.) with 10% FBS (HyClone Labs. Inc.).
Group 6. Ten µl of freshly prepared plasma added to 3 ml of D5648 tissue culture media (Sigma Inc.) with 10% FBS (HyClone Labs. Inc.).

The experiment was run in duplicate. Uninoculated media were used as a control. Samples were analyzed by dark-field and scanning electron microscopy at the time points of 0, 2, 4, 8, and 13 days.

Optical observation of proteons was performed with an OLYMPUS™ microscope fitted with a 100-W mercury lamp illumination source, a polarizer, a Naessens dark-field condenser (COSE Corp., Canada) and a 100× objective (oil, NA 1.4). The dark-field images were directed to a DEI-470T™ microscope video camera (Optronics Engineering, CA) utilizing the methods described in Vodyanoy et al. (1994) Langmuir 10:1354-1357. A direct count of proteons was used to determine their concentrations in liquid samples, and IMAGE PRO™ software (Creative Software, Inc.) was used to quantify the number of proteons.

The number of proteons incubated at 37° C. in an atmosphere of ambient air (Group 1) measured by dark-field microscope did not change significantly ($p<0.01$) during 13 days (FIG. 2A, line 1). The plasma at the same conditions (Group 2) showed a very small increase in population of proteons within 8 days of incubation, but the number increased dramatically and reached the number of proteons in group 1 after 13 days of incubation (FIG. 2A, line 2). Proteons and plasma in tissue culture media (Group 3 and 4, respectively) exhibited the same growth curves and reached the same number of proteons after 13 days of incubation (FIG. 2B). The culture media alone incubated at the same conditions showed no proteons (FIG. 2B, bottom line). No significant ($p<0.01$) effect of $CO_2$ was observed.

EXAMPLE 4

Reversibility of Construction and Deconstruction of Proteons In Vitro

Plasma was prepared as described in Example 1. The samples of plasma were combined with the guanidine hydrochloride or urea to a final concentration of 0, 0.01, 01, 1, 4, and 8 M, respectively. These chaotropic compounds are known to unfold and denature proteins.

Samples were subjected to heat of 120° C. and pressure of 20 psi. In the samples to which no chaotropic compounds were added, the numbers of proteons observed by dark-field microscopy was normally high. The number of proteons decreased as the concentration of chaotropic compounds was increased (FIG. 2C).

Samples of proteons grown at the suppressive presence of 8 M urea were subjected to dialysis using a Pierce Chem. Co. SLIDE-A-LYSER™ 10K dialysis cassette (20 h, 5 L, 20° C.) according to the manufacturer's instructions. The number of proteons found by dark-field microscope increased significantly. Samples of plasma treated with 120° C. heat d 20 psi pressure and urea at concentrations of 0.01-8 M were taken. Polyacrylamide gel electrophoresis was carried out on each sample with a 4-20% Tris-HCl READY™ precast gel (Bio-Rad Labs. Inc.) according to the manufacturer's protocol. The control (proteons without chaotropic compounds) showed two characteristic bands of 14,400 and about 8,000 D. The experimental samples (proteons in the presence of a chaotropic compound) displayed a diffuse distribution of proteins or fragments of proteins with no sharp bands of proteins of the high molecular mass range. As the concentration of urea increased, the intensity of the diffusion staining decreased, and almost fully disappeared at the 8 M concentration of urea. The proton sample displays a 14,400 D band that coincides with a similar band found in plasma. When guanidine hydrochloride or urea was added to proteons produced without the chaotropic compounds, heat of 120° C. and pressure of 20 psi resulted also in a great reduction of number of proteons visible by dark-field microscopy. Dialysis of these samples restored the population of the proteons. Gel electrophoresis of proteons and plasma treated with 120° C. heat and 20 psi pressure at the presence of urea, and then dialyzed, reveals two bands of 14,400 and about 8,000 D in all samples, including those before and after dialysis.

EXAMPLE 5

Effect of Ultrafiltration on Proteon Formation

PNCs were removed from blood plasma by filtering the plasma through 5 kD CENTRICON™ filters (Millipore Corp.) according to the manufacturer's protocol. The protein level in the retentate was quantitated and compared to that of unfiltered plasma Assay kits were obtained from Bio-Rad Laboratories, and quantitative studies were carried out according to the manufacturer's instructions. The amount of protein in the filtered plasma was the same as that measured in the non-filtered sample. No protein was detected in the filtrate. After filtration, proteons could not be produced until the filtered fraction was returned to the plasma. The number of proteons was dependent on the amount of filtrate returned to the retentate. Addition of 10 mM of the chelating agent, ethylene diamine tetra acetate (EDTA), known to form strong complexes with metals, also prevented the formation of proteon. Adsorption spectra of the filtrate, determined by energy dispersive x-ray spectroscopy (EDS) and inductively coupled plasma-atomic emission spectrometry (GTW Analytical Services, TN), revealed the presence of metals, including Cu, Zn, and Fe.

EXAMPLE 6

Analysis of PNCs

To characterize the nature of the PNC nanoparticles, transmission electron microscopy (TEM) was utilized. Transmission electron microscopy (TEM) was performed using a JEM 2010™ instrument (JEOL Ltd.), operated at 200 kV. Bright-field (BF), imaging was used to provide an overview of the microstructure of the sample. Features of interest were characterized by selected area diffraction (SAD) and nanobeam diffraction (NBD), with the latter set up to produce a narrow (<50 nm diameter), yet near-parallel beam, so that SAD-like patterns were produced. Dark-field (DF) imaging was employed to determine which microstructural features gave rise to the diffraction maxima. The composition of microstructural features was determined (qualitatively) by means of energy dispersive x-ray spectroscopy (EDS). This work employed an ultra-thin window (UTW) detector (Oxford Instruments plc), attached to the JEM 2010™ instrument, together with an ISIS™ analyzer (Oxford Instruments plc).

Scanning electron micrographs were obtained using a JSM-840™ SEM system (JEOL Ltd.). Plasma from rabbit blood was filtered consecutively through a 30 kD and a 5 kD CENTRICON™ filter (Millipore Corp.) before heat treatment. PNCs were precipitated from the filtrate by 1.2 mM MgSO4 at pH 11.3 and transferred onto 400 mesh Ni/carbon grids (Electron Microscopy Sciences Co.). Proteon samples for TEM were fixed with 3% gluteraldehyde, dehydrated with ethanol, and embedded in DURCUPAN™ ASM resin (Fluka Co.).

The bulk of the blood precipitate from rabbit plasma was amorphous. However, this extract was found to contain crystalline metallic nanoparticles, with diameters of around 1-2 nm and above. SAD patterns originating from different regions of the samples were consistent with the presence of both face centered cubic (FCC) and body centered cubic (BCC) metals (or possibly solid-solution alloys), with lattice parameters ($a_0$) of approximately 360 and 290 pin respectively. These combinations of Bravais lattice and ao are close to those of FCC copper ($a_0$=361.50 pm (International Centre Diffraction Data (2001), Powder Diffraction File, ICCD, Newtown Square, Pa.)) and BCC α-iron ("ferrite", $a_0$=286.64 pm (International Centre Diffraction Data (2001)), Powder Diffraction File, ICCD, Newtown Square, Pa.)), respectively. Furthermore, both copper and iron were encountered in EDS spectra acquired from the regions containing the nanoparticles. Centered DF imaging demonstrated that the diffraction maxima in these patterns originated from the nanoparticles. When viewed in BF, the metallic nanoparticles were very difficult to distinguish from the amorphous background in most regions of the samples. Hence, such particles could easily have been overlooked in the BF imaging techniques used conventionally for biological electron microscopy.

The observed crystallography of non-clumped nanoparticles was that of metallic iron and copper, rather than of salts of these metals. Furthermore, the diffraction patterns encountered in this work were not produced by an organometallic structure. The production of even nanometer-sized metallic particles implies the assembly of a significant number of metal atoms. For example, a 1 rim diameter Cu particle has the same volume as around 10 Cu, or 20 α-Fe, unit cells. FCC metals have 4 atoms per unit cell and BCC metals 2 atoms per cell, indicating a particle containing around 40 atoms in both cases (similarly, a 3 nm diameter particle would contain over 1,000 atoms).

Individual metallic nanoparticles had a random crystallographic orientation. Thus, in cases where the particles had become clumped (in some cases, this appeared to involve flocculation, in others some of the particles had sintered together), a polycrystalline aggregate was produced. In contrast, within a number of relatively large (around 10 rim diameter or above) clumps of particles, significant (~5-10 nm wide) regions were encountered with a constant crystallographic orientation. However, none of the clumps was a true single crystal. Some of these relatively large clumps contained a number of, as yet unidentified, second phases in addition to α-Fe and Cu.

Both Cu and Fe form stable oxides (for example the Gibbs free energy of formation of even the relatively low stability CuO phase is around −127 kJ mol$^{-1}$ at 300 K). See Brandes. and Brook (1992) *Smithells Metals Reference Book* (7$^{th}$ ed., Butterworth-Heinenmann, Oxford, UK). Furthermore, the initial stages of oxidation of these metals are rapid, even at room temperature. For example, logarithmic oxidation of initially bare iron, at an oxygen partial pressure of only 10 mPa, results in the growth of around 2 nm of oxide, after less than 20 minutes at 300 K. See Kruger, J and Yolken (1964), cited by Lawless. (1974) *Rep. Prog. Phys.* 37(2):231-316. The presence of non-noble metallic nanoparticles implies that the surrounding organic matrix has either impeded oxygen access to the metallic particles and/or has a significant reducing effect.

Many of the nanoparticles survived coarsening. The surface energy of the particles provides a driving force for larger particles to cannibalize smaller particles (the surface area to volume ratio for a 1-nm particle is 6×10$^9$ m$^{-1}$ and this drops by an order of magnitude for a 10-nm particle). Metallic materials have relatively high solid vapor interfacial energies ($\gamma_{SV}$) and those for copper and α-iron are around the middle of the range for metallic materials (at ~2.2 and 3.2 J m$^{-2}$, respectively; Murr (1975) *Interfacial Phenomena in Metals and Alloys* (Addison-Wesley; reprinted by TechBooks, Herdon, Va.)). Thus unless the metal—organic matrix interface has an interfacial energy ($\gamma_{SM}$) that is such that $\gamma_{SM} \ll \gamma_{SV}$, there would remain a significant thermodynamic driving force for coarsening. Given the kinetics of coarsening, if all that were present were the metallic nanoparticles, room-temperature coarsening would occur at a negligible rate (solid-state sintering involves bulk diffusion, interfacial diffusion, free surface diffusion and evaporation and re-condensation, all of which would be very slow for Cu or α-Fe at room temperature). See Ashby (1974), *Acta Metallurgica* 22(3):275-289. See also, Swinkels and Ashby (1981) *Acta Metallurgica* 29(2):259-281. Although the presence of the organic liquid matrix raises possibilities for mass transport, it appears that the matrix did not provide a path for the rapid transfer of metal atoms since many of the nanoparticles of served in the present work remained extremely fine.

EXAMPLE 7

In Vitro Effect of PNC on Cultured Cells

The impact of PNCs upon viability of various cultured cells was investigated using the tetrazolium salt (MTT) cell proliferation assay. RG2 (mouse brain glioma), F98 (rat brain glioma), Hs683 (human brain glioma), CTX TNA2 (rat transfected astrocyte), H9c2[2-1] (rat heart myocardium), 27FR (rat skin fibroblast), and SVGp12 (human brain astroglia) cells were obtained from American Type Culture Collection (ATCC) and maintained as recommended by ATCC. MTT cell proliferation assays are commercially available. See, e.g., MTT cell proliferation assay from ATCC.

Cells were plated in Dulbecco's modified Eagle's growth medium (D5648, Sigma Chemical Inc., St. Louis, Mo.) +10% fetal bone serum (FBS) (Hyclone Laboratories, Logan, Utah) in polystyrene 96-well plates at a density 3×10$^3$ cells per well. Twenty-four hours after plating, the medium was replaced with DMEM with either staurosporine (100 µl, 1 µM) or PNC (aliquots, 100 µl, 5×10$^9$–3×10$^{11}$ PNC/ml). PNCs were isolated from blood obtained from shark, dog, and rabbit using the ultrafiltration protocol described in Example 5. PNCs were autoclaved at 120° C. and 20 psi for 15 minutes before adding to the cell cultures.

After 20 hours of treatment, a 20-µl aliquot of tetrazolium salt (MTT, 5 mg/ml in PBS) was added to the wells, and interaction was allowed to proceed for 4 hours at 37° C. MTT was reduced in metabolically active cells to form purple formazan crystals, which were dissolved by DMSO and quantified by a BIO-RAD™ plate reader. For each cell type, a linear relationship between cell number and absorbance is established, enabling accurate, straightforward quantification of changes in proliferation.

In two trials, the effect of PNCs on RG2 cells was studied utilizing the following protocol:

Day 1.
  Plate out RG2 cells at a density of 3×103 cells/well in D5648+10% FCS and incubate overnight.
  Staurosporine (Sigma Inc. Catalog No. S5921), 100 µg, FW 466.5. Dissolve 100 µg staurospine into 214.3 µl DMSO to equal a 1 mM stock solution. Store at –200° C. Dilute stock 1:10 in media to equal 0.1 mM or 100 µM stock.
Dilute as follows:
466.5 gm/1 liter=1 M
100 µg/2.143 ml=100 µM (frozen stock)
  use 10 µl/well=1 µM
Day 2.
Remove media and add DMEM+1% FCS (100 µl/well). TX put on late afternoon.
  Add staurospine, autoclaved shark PNC, and either 10%, 1%, or 0% FCS treatments to cells and incubate overnight.

The results of this study are shown in Tables 6 and 7, below. (Ab. Av. _Absorbance at 550 nm; St. Dv.=Standard Deviation)

TABLE 6

MTT assay on RG2 glioma cells, with 10%, 1% and 0% FCS

Shark Seeds-autoclaved

| Shark 3 | 10% FCS no tx | 10% FCS 20 µl | 10% FCS 10 µl | 10% FCS 1 µl | 1% FCS no tx | 1% FCS 20 µl | 1% FCS 10 µl | 1% FCS 1 µl | 0% FCS no tx |
|---|---|---|---|---|---|---|---|---|---|
| | 0.533 | 0.298 | 0.404 | 0.482 | 0.731 | 0.408 | | | 0.866 |
| | 0.542 | 0.316 | 0.414 | 0.465 | 0.753 | 0.433 | 0.544 | 0.724 | 0.891 |
| | 0.577 | 0.374 | 0.425 | 0.526 | 0.74 | 0.394 | 0.533 | 0.605 | 0.695 |
| | 0.516 | 0.369 | 0.409 | 0.467 | 0.633 | 0.365 | 0.596 | 0.633 | 0.937 |
| | 0.5 | 0.321 | 0.431 | 0.466 | 0.684 | 0.411 | 0.571 | 0.612 | 0.799 |
| | | 0.362 | 0 414 | | 0.693 | 0.419 | 0.541 | | 0.909 |
| | | 0.285 | 0.373 | | 0.636 | 0.384 | 0.573 | | 0.928 |
| | | 0.297 | 0.393 | | 0.637 | 0.431 | 0.529 | | 0.949 |
| Ab. Av | 0.5336 | 0 32775 | 0.40787 | 0.4812 | 0.688375 | 0.40562 | 0.54787 | 0.6562 | 0.87175 |
| St. Dv. | 0.02912 | 0.03556 | 0.01834 | 0.02599 | 0 049494 | 0.02348 | 0.03119 | 0.05543 | 0.085951 |

| Shark 3 | 0% FCS 20 µl | 0% FCS 10 µl | 0% FCS 1 µl | staurosporine 10% FCS 1 µM | 10% FCS water 20 µl | 1% FCS water 20 µl | 0% FCS water 20 µl |
|---|---|---|---|---|---|---|---|
| | 0.432 | 0.739 | 0.827 | 0.406 | 0.436 | 0.726 | 0.971 |
| | 0.464 | 0.653 | 0.895 | 0.411 | 0.46 Z | 0.701 | 0.74 |
| | 0.463 | 0.713 | 0.918 | 0.399 | 0.394 | 0.676 | 0.79 |

TABLE 6-continued

| MTT assay on RG2 glioma cells, with 10%, 1% and 0% FCS | | | | | | |
|---|---|---|---|---|---|---|
| | 0.429 | 0618 | 0.833 | | | |
| | 0.463 | 0.638 | 0.78 | | | |
| | 0.479 | 0.677 | | | | |
| | 0.452 | 0.577 | | | | |
| | 0.551 | 0.574 | | | | |
| Ab. Av | 0.466625 | 0.64862 | 0.8506 | 0.405333 | 0.430667 | 0.70 | 0.8313667 |
| St. Dv. | 0.038049 | 0 05962 | 0.05559 | 0.006028 | 0.034312 | 0.02 | 0125.153 |

TABLE 7

MIT assay, RG2 cells in 1% FCS, with shark, rabbit and dogs 1 and 2 seeds, autoclaved.

| | no tx | 20 μl | 10 μl Shark Seeds | 1 μl | 20 μl | 10 μl Dog 1 seeds | 1 μl |
|---|---|---|---|---|---|---|---|
| | 0.64 | 0.342 | 0.447 | 0.664 | 0.675 | 0.773 | 0.658 |
| | 0.694 | 0.344 | 0.616 | 0.596 | 0.633 | 0.705 | 0.598 |
| | 0.667 | 0.373 | 0.407 | 0.595 | 0.527 | 0.662 | 0.712 |
| | 0.678 | 0.322 | 0 499 | 0 676 | 0.57 | 0.613 | 0.625 |
| | 0.675 | | | 0.626 | 0 63 | 0.63 | 0.625 |
| | | | | 0.634 | 0.728 | 0.675 | 0.639 |
| | | | | 0.689 | | 060.7 | 0.688 |
| | | | | 0 596 | 0.719 | 0.629 | 0 61 |
| Ab Av. | 0.6708 | 0.34525 | 0.49225 | 0.6345 | 0.63525 | 0 67375 | 0 644375 |
| St. Dv. | 0.019817 | 0.020998016 | 0.090691326 | 0.038097619 | 0.07015035 | 0.05268437 | 0.03923168 |

| | 20 μl | 10 μl Dog 2 seeds | 1 μl | 20 μl | 10 μl Rabbit seeds | 1 μl | stauro 1% FCS |
|---|---|---|---|---|---|---|---|
| | 0.555 | 0 595 | 0.687 | 0.503 | 0.62 | 0.732 | 0.108 |
| | 0.568 | 0.642 | 0.541 | 0.582 | 0.577 | 0 676 | 0 095 |
| | 0.543 | 0.65 | 0.601 | 0 476 | 0.607 | 0.589 | 0.093 |
| | | 0529 | 0.534 | 0 512 | 0.6 | 0.647 | |
| | 0.561 | 0.53 | 0.66 | 0.585 | 0.564 | 0.64 | |
| | 0.526 | 0.638 | 0.623 | 0.584 | 0.604 | 0.61 | |
| | 0.498 | 0.593 | 0.644 | 0.565 | 0.519 | 0 634 | |
| | 0.566 | 0.658 | 0.559 | 0.536 | 0 554 | 0.649 | |
| Ab Av. | 0.54325 | 0.61925 | 0.606125 | 0.542875 | 0.580625 | 0.647125 | 0.09866667 |
| St. Dv. | 00240294326 | 72887 | 0.05713752 | 0.0423402 | 0.03372976 | 0.0431 92 | 0.00814453 |

Figure 2:
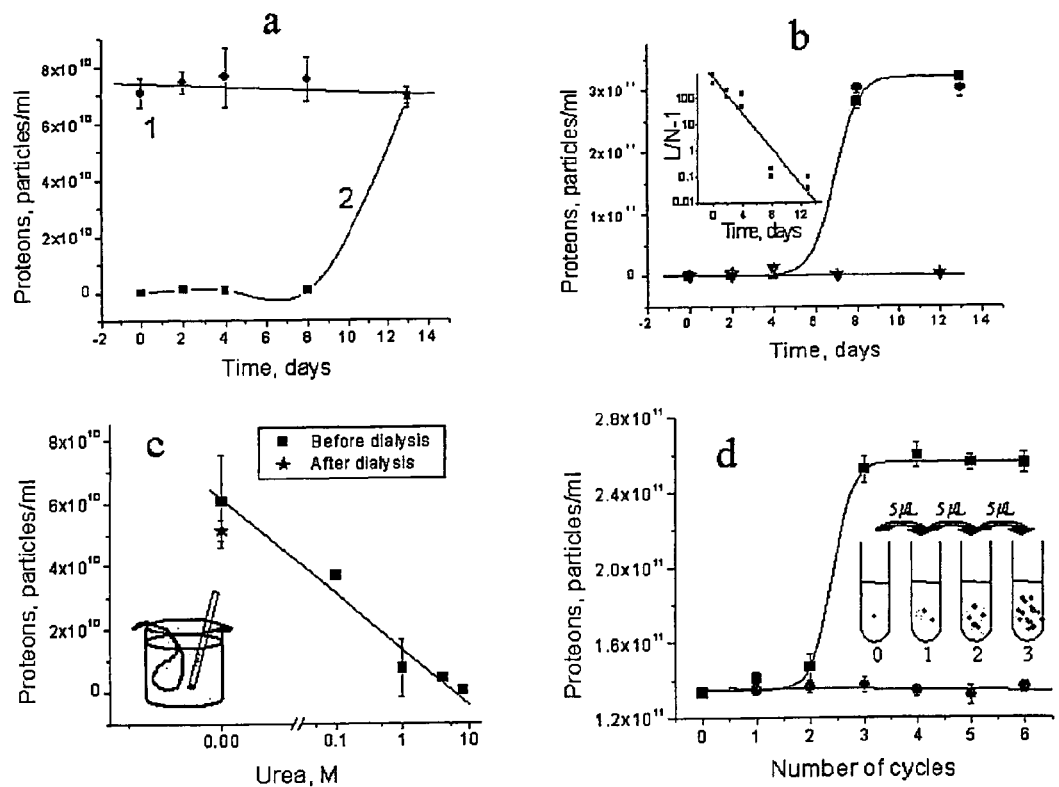
Figure 3:
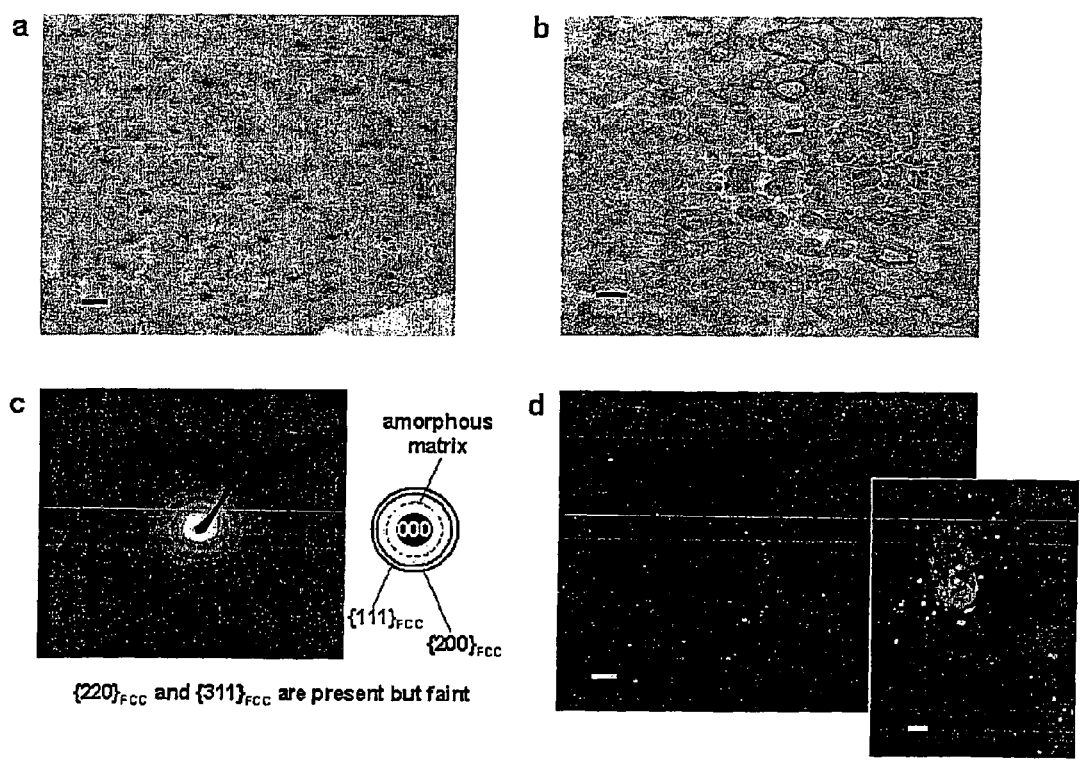
Figure 4:
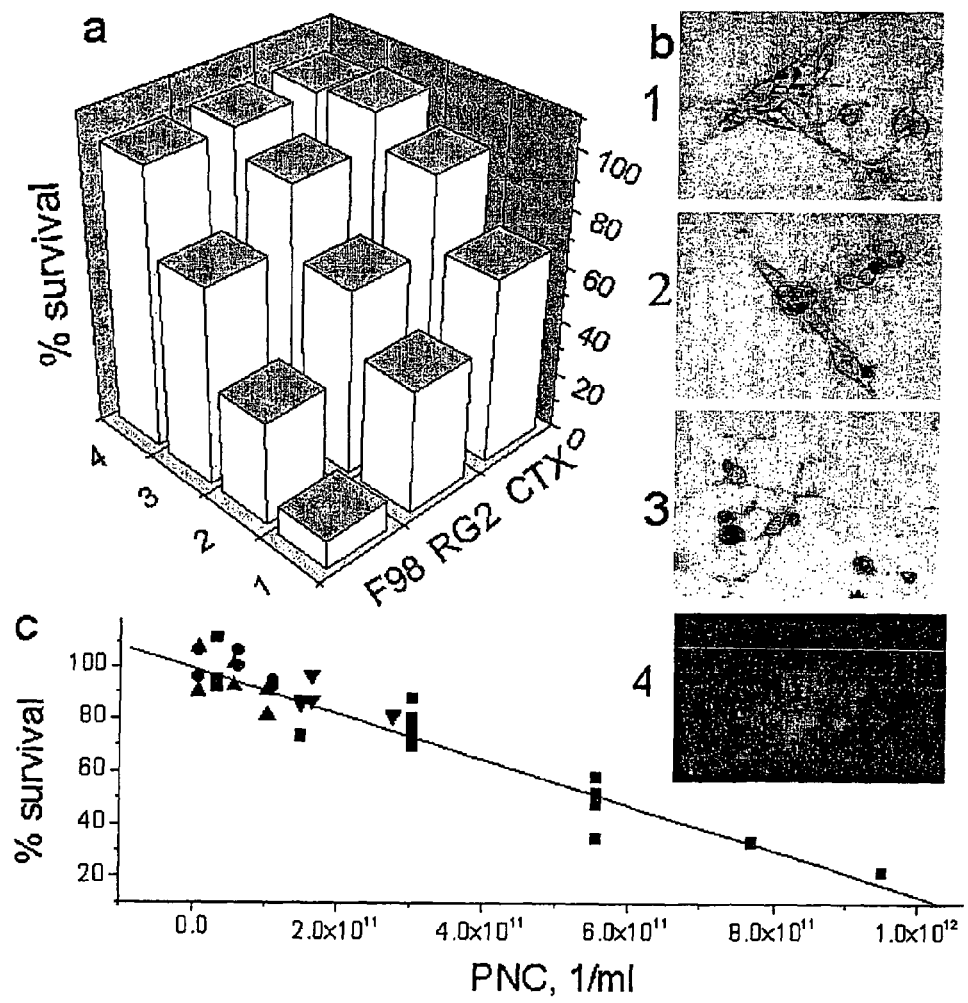

Similar studies were carried out comparing the effect of shark PNCs with staurosporine. See Tables 8-10, below. A significant decrease in cell viability was observed for cultured cells incubated with PNCs for 20 hours (FIG. 4A). The viability of the rat and mouse-glioma cells—declined by 90% and 75%, respectively, while the viability of the rat ostrocytes decreased by only 25% at the same conditions. Post-exposure morphological observations of cells under optical dark-field microscope showed signs of cell death. Cells were shrunk and rounded, nuclei were condensed and showed budding of cell bodies (FIG. 4B-2). Cell damage produced by the shark PNCs compares well with the injury made by 1 μM of staurosporine (a potent apoptosis inducing reagent) (FIG. 4B-3). A significant effect on cell viability was also observed with Hs683 (human brain glioma), H9c2[2-1] (rat heart myocardium), 27FR (rat skin fibroblast), and SVGp 12 (human brain astroglia) cells. Proteons and PNCs obtained from the blood plasma of healthy dog and rabbit also significantly affected the viability of the cultured mammalian cells.

FIG. 4C shows the viability of RG2 glioma cells exposed to PNCs from different sources. It takes about $1 \times 10^{12}$ PNC/ml to fully suppress these glioma cells. This concentration accounts for not more than 10% of the full concentration of PNCs in a healthy animal.

TABLE 8

| MTT assay on various cell lines with shark seeds and 0% FCS | | | | | | | | |
|---|---|---|---|---|---|---|---|---|
| | RG2 | | | | Fibroblast | | | |
| | No Tx | 1 μl | 10 μl | 20 μl | No tx | 1 μl | 10 μl | 20 μl |
| Plate 1 0% FCS | 1.075 | 0.964 | 0.856 | 0.597 | 0.658 | 0.503 | 0.595 | 0.342 |
| | 1.169 | 1.014 | 0.791 | 0.496 | 0.603 | 0.517 | 0.541 | 0.36 |

TABLE 8-continued

MTT assay on various cell lines with shark seeds and 0% FCS

|  | | | | | | | | |
|---|---|---|---|---|---|---|---|---|
|  | 1.103 | 1.016 | 0.688 | 0.523 | 0.523 | 0.558 | 0.492 | 0.375 |
|  | 1.084 | 1.082 | 0.739 | 0.55 | 0.556 | 0.569 | 0.432 | 0.382 |
| Ab. Av. | 1.10775 | 1.019 | 0.7685 | 0.5415 | 0.59375 | 0.53625 | 0.515 | 0.36475 |
| St. Dv. | 0.042463 | 0.048401 | 0.07191 | 0.04307 | 0.048016 | 0.031298 | 0.069508 | 0.017727 |

|  | Myocard | | | | CTX astrocytes | | | |
|---|---|---|---|---|---|---|---|---|
|  | No tx | 1 µl | 10 µl | 20 µl | No tx | 1 µl | 10 µl | 20 µl |
| Plate 1 0% FCS | 0.509 | 0.452 | 0.496 | 0.376 | 0.622 | 0.596, | 0.555 | 0 429 |
|  | 0.462 | 0.373 | 0.471 | 0.382 | 0.603 | 0.589 | 0.559 | 0.489 |
|  | 0.494 | 0.438 | 0.462 | 0.33 | 0.59 | 0.645 | 0.561 | 0.396 |
|  | 0.449 | 0.446 | 0.513 | 0.309 | 0.565 | 0.6 | 0.533 | 0.434 |
| Ab. Av. | 0.4785 | 0.42725 | 0.4855 | 0.34925 | 0.595 | 0.6075 | 0.552 | 0.42725 |
| St. Dv. | 0.027767 | 0.036619 | 0.023302 | 0.035491 | 0.02393 | 0.02541 | 0.01291 | 0.038549 |

|  | SVG astrocytes | | | | F98 glioma | | | |
|---|---|---|---|---|---|---|---|---|
|  | No tx | 1 µl | 10 µl | 20 µl | No tx | 1 µl | 10 µl | 20 µl |
| Plate 1 0% FCS | 0.678 | 0.688 | 0.441 | 0.275 | 1 045 | 0.914 | 0.367 | 0.213 |
|  | 0.681 | 0.585 | 0.439 | 0.275 | 0.977 | 0.697 | 0.444 | 0.16 |
|  | 0.676 | 0.587 | 0.462 | 0.251 | 0.966 | 0.643 | 0.415 | 0.196 |
|  | 0.656 | 0.667 | 0.363 | 0.244 | 1.064 | 0.73 | 0.504 | 0.172 |
| Ab. Av. | 0.67275 | 0.63175 | 0.42625 | 0 26125 | 1.013 | 0.746 | 0.4325 | 0.18525 |
| St. Dv. | 0.011354 | 0.053525 | 0.043431 | 0.016132 | 0.048751 | 0.117601 | 0.057274 | 0.023796 |

TABLE 9

MTT assay on various cell lines with shark seeds and 1% FCS

|  | RG2 | | | | Fibroblast | | | |
|---|---|---|---|---|---|---|---|---|
| Plate 2 | No tx | 1 µl | 10 µl | 20 M1 | No tx | 1 µl | 10 µl | 20 µl |
| 1% FCS | 0.839 | 0.6.06 | 0.536 | 0.3.6 | 0.503 | 0.44 | 0.5 | 0.307 |
|  | 0.734 | 0.551 | 0.723 | 0.419 | 0.475 | 0.452 | 0.44 | 0.316 |
|  | 0.665 | 0.595 | 0.551 | 0.435 | 0.465 | 0.58 | 0.351 | 0.298 |
|  | 0 723 | 0.656 | 0.564 | 0.445 | 0.457 | 0.547 | 0.308 | 0.371 |
| Ab Av | 0.74025 | 0.602 | 0.5935 | 0.4145 | 0.475 | 0.48925 | 0.39975 | 0 323 |
| St Dv | 0.072459 | 0.043135, | 0.087088 | 0.038038 | 0.020067 | 0 01558 | 0.086535 | 0.032833 |

|  | Myocard | | | | CTX astrocytes | | | |
|---|---|---|---|---|---|---|---|---|
| Plate 2 | No tx | 1 µl | 10 µl | 20 M1 | No tx | 1 µl | 10 µl | 20 µl |
| 1% FCS | 0.404 | 0 43 | 0.37 | 0.317 | 0.521 | 0.501 | 0.501 | 0.355 |
|  | 0.43 | 0.444 | 0.349 | 0 326 |  | 0.564 | 0.426, | 0.415 |
|  | 0.408 | 0.466 | 0.326 | 0.289 | 0.542 | 0.562 | 0.42 | 0.387 |
|  | 0.425 | 0.458 | 0.321 | 0.377 | 0 538 | 0.641 | 0.439 | 0.471 |
| Ab Av | 0.41675 | 0.4495 | 0 32825 | 0.32725 | 0 527 | 0.567 | 0.4465 | 0.407 |
| St Dv | 0.012685 | 0.015864 | 0.014315 | 0 036719 | 0.016145 | 0.057347 | 0.037189 | 0.049207 |

TABLE 9-continued

MTT assay on various cell lines with shark seeds and 1% FCS

| | SVG astrocytes | | | | F98 glioma | | | |
|---|---|---|---|---|---|---|---|---|
| Plate 2 | No tx | 1 μl | 10 μl | 20 μl | No tx | 1 μl | 10 μl | 20 μl |
| 1% FCS | 0.602 | _0.09 | 0.352 | 0 248 | 0 746 | 0.687 | 0 376 | 0.137 |
| | 0.597 | 0 496 | 0.37 | 0.238 | 0.971 | 0.524 | 0.334 | 0.154 |
| | 0.534 | 0.488 | 0.40 | 0.246 | 0.91 | 1 267 | 0.283 | 0.41 |
| | 0.48 | 0 547 | 0.394 | 0.26 | 0.864 | 0.521 | 0.309 | 0.139 |
| Ab Av | 0.55325 | 0.51 | 0.37925 | 0.248 | 0.87275 | 0.74975 | 0.3255 | 0.14275 |
| St Dv | 0.057812 | 0.026141 | 0.0225 | 0.009092 | 0.095189 | 0.353447 | 0.039585 | 0.007676 |

TABLE 10

MTT assay on various cell lines with Staurosporine

| Saurosp | RG2 100 urn | RG2 | Fibro | Fibro | Myocard | myocard |
|---|---|---|---|---|---|---|
| Shark 7 | 0.305 | 0.12 | 0.257 | 0.168 | 0.402 | 0.154 |
| | 0.301 | 0.119 | 0.275 | 0.166 | 0.373 | 0.151 |
| Plate 3 | 0.279 | 0.119 | 0.275 | 0.171 | 0.172 | 0.159 |
| 1% FCS | 0.272 | 0.149 | 0.296 | 0.171 | 0.185 | 0.176 |
| Ab. Av. | 0.28925 | 0.12675 | 0.27575 | 0.169 | 0.283 | 0.16 |
| St. Dv. | 0.016215 | 0.014841 | 0.015945 | 0.002449 | 0.121362 | 0.011165 |

| Saurosp | CTX astro | CTX astro | SVG astro | SVG astro | F98 glioma | F98 glioma |
|---|---|---|---|---|---|---|
| Shark 7 | 0.252 | 0.212 | 0.128 | 0.067 | 0.136 | 0.108 |
| | 0.518 | 0.122 | 0.12 | 0.066 | 0.138 | 0.108 |
| Plate 3 | 0.533 | 0.118 | 0.128 | 0.067 | 0.12 | 0.109 |
| 1% FCS | 0.21 | 0.126 | 0.136 | 0.068 | 0.139 | 0.109 |
| Ab. Av. | 0.37825 | 0.1445 | 0.128 | 0.067 | 0.13325 | 0.1085 |
| St. Dv. | 0.171002 | 0.045118 | 0.006532 | 0.000816 | 0.008921 | 0.000577 |

EXAMPLE 8

Cyclic Amplification of Proteons

A progressively increased number of proteons can be produced from plasma subjected to increasing temperatures. To examine a method of cyclic amplification, seven 1 ml samples of plasma were prepared for cyclic amplification. After e intia number of proteons was quantitated by a dark-field microscope, the first sample was incubated for 15 minutes at 65° C. and normal pressure. Five μl of the treated first sample was introduced to seed the untreated second sample, and the second sample was incubated for 15 minutes at 65° C. and normal pressure. This step was repeated: 5 μl of the second amplified sample was added to the third untreated sample. This process was repeated up to 6 cycles. A control series was run by adding of five μl of purified water (instead of seeds) to 1 ml of untreated plasma.

The first two cycles resulted in a small but significant ($p<0.001$) increase of proteon population, whereas the third cycle brought about a dramatic increase in the number of proteons. The next three cycles resulted in saturation of the proteon population. In contrast, the control samples showed no dramatic increase of the proteon population. See FIG. 2.

EXAMPLE 9

Comparison with Other Biological Particles

Experiments were carried out to compare the proteons obtained by the procedure described in the Example 1 with nanobacteria isolated from blood by Kajander et al. (1996) Mol. Biol. Cell 7:3007-3007 using the NANOCAPTURE™ enzyme linked immunosorbent assay (ELISA) kit for detection of nanobacterial antigens (Nanobac OY, Finland). The nanobacteria included in the NANOCAPTURE™ ELISA kit were used as a positive control. The BIO-RAD MICROPLATE MANAGER™ 4.01 software (Bio-Rad Labs. Inc.) was used to obtain the results of the ELISA. The assay procedure was carried out following the manufacturer's recommendations. The reaction was considered to be positive when the absorbance was significantly higher then the level of noise. Results of interaction of antibodies grown against nanobacteria with proteons and plasma are summarized in Table 11.

TABLE 11

Interaction of antibodies specific to nanobacteria with proteons and plasma.

| No | Sample | Condition | Reaction |
|---|---|---|---|
| 1 | Proteons, human 1 | Freshly prepared at 120° C. and 20 psi, 2 h | − |
| 2 | Proteons, human 2 | Freshly prepared at 120° C. and 20 psi, 2 h | − |
| 3 | Proteons, rabbit | Freshly prepared at 120° C. and 20 psi, 2 h | − |
| 4 | Proteons, human 1 | Incubated 13 days, 37° C. | − |
| 5 | Plasma, human | Incubated 13 days, 37° C. | − |
| 6 | Plasma, human 1 | Incubated 13 days, 37° C. | − |
| 7 | Proteons, human 1, in D5648[a] | Incubated 13 days, 37° C. | + |
| 8 | Proteons human 1, in D6429[b] | Incubated 13 days, 37° C. | + |
| 9 | Plasma, human 1, in D5648[a] | Incubated 13 days, 37° C. | + |
| 10 | Plasma, human 1, in D6429[b] | Incubated 13 days, 37° C. | + |
| 11 | Proteons, human 1, in D5648[a] | Incubated 13 days, 37° C. | + |
| 12 | Proteons human 1, in D6429[b] | Incubated 13 days, 37° C.; 5% $CO_2$-95% air | + |
| 13 | Plasma, human 1, m D5648[a] | Incubated 13 days, 37° C.; 5% $CO_2$-95% air | + |
| 14 | Plasma, human 1, in D6429[b] | Incubated 13 days, 37° C.; 5% $CO_2$-95% air | + |
| 15 | Proteons, human 1, in D5648[a] | Incubated 13 days, 37° C.; 5% $CO_2$-95% air | + |
|  | D5648[a] | Incubated 13 days, 37° C. | + |
|  | D6429[b] | Incubated 13 days, 37° C. | + |
| 16 | D6429[b] | Freshly prepared | − |
| 17 | Water[c] | Freshly prepared | − |
| 18 | Broth[d] | 120° C. and 20 psi, 2 h | − |
|  | Nanobacteria |  | + |

[a]D5648 tissue culture media (Sigma Inc.) with 10% FBS (HyClone Labs. Inc.).
[b]D6429 tissue culture media (Sigma Inc.) with 10% FBS HyClone Labs. Inc.).
[c]Purified water (Direct QTM, Millipore Corp., 17 MOhm)
[d]LB-Medium (BIO 101, Inc.; 10 g Trypton-B, 5 g yeast extract-B, 10 h NaCl in 1 L of water).

Nanobacteria gave a positive signal, while all freshly prepared proteons showed no interaction. Proteons incubated in cell culture media for 13 days, at 37° C. (with and without C02) show a positive reaction. However, the culture media alone incubated for 13 days, at 37° C. also gave a positive reaction, while freshly prepared culture media was negative, indicating that nanobacteria antigen appeared from the culture media during the incubation.

EXAMPLE 10

A. Objectives

The central objective of this example is to show that the stable inorganic nuclei control misfolding and aggregation of prion-related proteins. To that end, it is desired to define molecular mechanisms of interaction of proteins and nuclei during the process of assembling and proliferation of misfolded protein particles. A further object is to show that metals are involved in the natural folding and misfolding of proteins. The metals are not in ion state, but rather in the clusters of metal atoms. These atoms are directly bonded to each other creating a polyatomic metallic nucleus. We propose to use protein particles found in blood and recombinant prion protein particles as working in vitro models. The rationale that underlies this example is that prions belong to the class of misfolded proteins. Their natural replication is slow and concentration available for antemortem tests is small. We propose an in vitro method of artificial acceleration of replication of misfolded proteins that allows a rapid transition of proteins from normal to abnormal state in the presence of small quantities of natural or artificial seeds. After amplification, when the amount of misfolded proteins is high, it can be detected and identified by conventional methods. This method can be adapted for an antemortem diagnostics of prions in biological fluids. Our goal is to develop the method of amplification and control of misfolded protein proliferation for diagnostic and treatment of prion-related and other conformational disorders Aim 1. Determine conditions controlling assembling and disassembling of protein particles (proteons).
a. Perform assay of proteon amplification at different physical and chemical conditions:
1. temperature at the range of 30-120° C., normal pressure at the temperatures below 100° C., and elevated pressures up to 20 psi at temperatures between 100 and 120° C., different time of assay,
2. natural and artificial seeds;
3. chaotropic compounds, such as guanidine hydrochloride and urea;
4. chelating agents such as EDTA, EGTA and EDPA;
5. inhibitory compounds like creosote;
6. protective compounds like trehalose, sucrose and raffinose.
b. Perform assay of cyclic proteon amplification at 65° C. with addition of natural and artificial PNCs.
1. Proteins from blood;
2. Protein from yeast;
3. Prion protein Aim 2. Define and characterize properties of protein nucleating particles (PNCs) participating in misfolding, polymerization, and aggregation of proteins.
a. Separate PNC and proteins by chemical and physical methods:
1. SDS polyacrylamide-gel electrophoresis;
2. chelating resin column;
3. chaotropic compounds;
4. dry ashing with an electric furnace, microwave, and oxygen plasma.
b. Determine structure and composition of protein particles and PNCs by electron microscopy techniques, energy dispersive X-ray spectrometry, and X-ray diffraction,
c. Prepare PNCs purified from plasma and artificial PNCs using information obtained in Aim 2b; use metallic nanaparticles as model systems.

B. Background and Significance

There are many disorders that are thought to arise from the same general mechanism based upon misfolding and then aggregation of underlying proteins. The group of so called conformational disorders includes many known prion-related disorders, most of the neurodegenerative diseases, and also several systemic disorders (Schluter and Drenckhahn, 1986; Kannan et al., 1988; Carrell and Lomas, 1997; Carrell and Gooptu, 1998; Soto, 2001; Jaikaran and Clark, 2001; Ursini, et al., 2002; Davis et al., 2002; Ursini, et al., 2002; Thompson and Barrow, 2005). One of the suggested mechanisms of the protein aggregation is based on the seeded polymerization in which initial seeds nucleate the deposition of monomers (Borchsenius et al., 2001). Heinz bodies, aggregates of denatured hemoglobin were found in aged erythrocytes (Schluter and Drenckhahn, 1986). Another protein aggregation found in blood comes from sickle erythrocytes and mostly composed of globin (Kannan, et al., 1988). Particles resembling ones described by Enderlein, 1925, were found in blood of cancer patients and claimed to be composed mostly of denatured albumin and hemoglobin (Garner, 1997). The presence of small particles of 0.1-5 microns the authors named nanobacteria, was found in biological systems (Kajander, 1992, Kajander et al., 1996, 2001; Kalander and Ciftcioglu, 1998. Ciftcioglu and Kajander, 1998; Ciftcioglu, at al., 1996, 1999, 2002; Garcia Cuerpo, et al., 2000; Hjelle, et al., 2000; Vali, et al., 2001). Nanobacteria have also been claimed to be found in minerals (Folk and Lynch, 1997; Folk and Lynch, 1999; Folk and Lynch, 2001; Folk, 1994, Folk, 1996, Folk 1997, Folk, 1999). A group of scientists from Sweden and Norway found micrometer-sized particles in cerebrospinal fluid (CSF) in patients with schizophrenia (Wetterberg, at al., 2002). Twenty years ago Prusiner (1982) described proteinaceous particles which caused scrapie, and ever since these particles and their structure are important subjects of prion diseases (Wille, et al., 2002; Geschwind, et al., 2002; Dyson, et al, 2002; Dourmashkin at al., 2004).

The rate of accumulation of misfolded proteins and aggregates causing these disorders are relatively small and it takes a long time from a few months to several years, before the decease produces noticeable dysfunction (Agguzzi, 2000, 2001). All methods of detection are challenged with a very small concentration of target materials. For example, the concentration of the misfolded prion protein in the brain of terminally ill hamsters is only about 0.1% (Beekes, at al., 1995). Amplification is needed because the amount of the misfolded prion protein available for tests in lymphoid system and blood is quite small (Agguzzl, 2001, Brown, et al., 2001; Wadsworth, et al., 2001). Most detection systems, such as immunohistochemistry or Western blotting, have been utilized for brain or lympho-reticular tissues (Madec, at al., 1998; MacGregor, 2001; Federspil, et al., 2002; Laffling, at al., 2002; Takekida, at al., 2002; Pan at al, 2005; Yuan et al., 2005). Detection of pathological molecular alterations in scrapie-infected hamster brain in the terminal and preclinical stages of disease was demonstrated by using Fourier transform infrared (FT-IR) spectroscopy (Kneipp, at al., 2000, 2002). Much less information is available for assays applied to blood, plasma, or other biological fluids, although some publications provide indications of their feasibility (Bieschke, et al, 2000, Agguzzi, 2001, Brown, at al., 2001; Wadsworth, et al., 2001; Ohtsuka at al., 2005; Yuan at al., 2005).

The mechanisms of prion replication are controversial. According the original idea the infectious agent, named prion, is represented solely by a protenateous particle (Prusiner, 1982, 1991; Griffith, 1967). In heterodimer mechanism of replication (Cohen, at al., 1994) a single misfolded prion protein molecule, $PrP^{SC}$, catalyses the conformational change of a single normal prion, $PrP^{C}$. According to the model of co-operative autocatalysis (Eigen, 1996, Laurent, 1997) a mixed aggregate of $PrP^{C}$ and $PrP^{SC}$ converts to an aggregate of $PrP^{SC}$ through allosteric interactions. According to nucleated polymerization (Eigen, 1996; Harper, et al., 1997; Jarrett and Lansbury, 1993) a seed of $PrP^{SC}$ is present and interact with $PrP^{C}$. When experimental data were compared with theoretical predictions of the above three mechanisms the nucleated (seeded) polymerization showed the best fit (Masel, et al., 1999). However, the mystery remains. What is the nature of the seed that catalyze the prion protein conversion (Tuite, 2000; Sparrer, at al., 2000). Sokolowski et al., 2003 found that formation of critical oligomers is a key event during conformational transition of recombinant prion protein. However it took a strong denaturant, 1 M guanidine hydrochloride at pH 4.2, and 25 days to grow 10-15 nm particles and 55 days to grow relatively short filaments from the hamster PrP. Trieschmann at al., 2005 found that the addition of preformed prion protein can facilitate propagation of misfolded prion protein. They hypothesized that the preformed aggregates functioned as seeds that facilitated the formation of new aggregates in plasma. About 6-fold increase of prion propagation was observed in seeded samples compared to those without seeds.

According to Tutte, 2000 comments to the protein seeds of prion propagation the physical agitation and presumed consequent fragmentation of prion aggregates greatly increased their seeding activity in vitro. The idea of physical agitation and fragmentation was fully explored a few years ago, when a method of cyclic amplification of misfolded protein was introduced (Saborio at al., 2001; Soto at al., 2002, 2005; Castilla et al., 2005, 2005a; Sea at al., 2005). The amplification cycle was composed of two steps. During the first step, a sample is incubated to grow polymers. In the second step the sample is subjected to ultrasound, as authors believe, to break down the polymer, multiplying the number of nuclei. In each cycle, brain homogenate was incubated for one hour and then sonicated with five pulses of 1 second each. These cycles were repeated 5-40 times. Consequently, the whole amplification procedure takes about 5-40 hours. It was reported that 140 amplification cycles led to a 6,600-fold increase in sensitivity over standard detection methods (Castilla et al., 2005). Another group has replicated and improved the cyclic amplification method and has reported 200,000-fold increase over 150 cycles (Sarafoff et al., 2005; Piening et al., 2005). But again, the whole amplification procedure took many hours.

There is substantial evidence that prion protein is a Cu-binding protein. In conversion to the misfolded form this Cu binding activity is lost. Instead, the protein binds other metals such as Mn or Zn (Brown, 2004). These facts are consistent with the observation that the in vitro cyclic amplification process is weakly facilitated by divalent cations such as Mn, Zn and Ni but not Cu (Sarafoff et al., 2005). Similar findings were indicating that transition metal ions bind prion proteins.

Significance.

We can conclude that there is great need for a fast and accurate antemortem diagnostics for prion-related and other conformational disorders. The ability to detect a very small number of the misfolded proteins in samples of blood, other fluid, and small samples of tissue, would constitute an effective method of antemortem diagnostics. Developing methods to efficiently amplify small amounts of misfolded proteins in these samples should have clinical importance. The most probable mechanism of prion propagation involves nucleated (seeded) polymerization and aggregation. Thus, it is believed that the method proposed herein can be adapted and used in the future for clinical diagnostics and treatment of prion related disorders.

C. Preliminary Studies

Summary.

Unfolding and subsequent aggregation of proteins is a common phenomenon that is linked to many human disorders. We isolated micrometer and sub-micrometer particles, termed proteons, from human and animal blood. Proteons lack nucleic acids but contain two major polypeptide populations with homology to the Hb α-chain. Proteons form by reversible seeded aggregation of proteins around protein nucleating centers (PNCs). PNCs are comprised of 1-2-nm metallic nanoclusters containing 40-300 atoms. Each milliliter of human blood contained $\sim 7 \times 10^{13}$ PNCs and $\sim 3 \times 10^{8}$ proteons. Exposure of isolated blood plasma to elevated temperatures increased the number of proteons. When an aliquot of this heated plasma was introduced into untreated plasma that subsequently heated, the number of proteons further increased, reaching a maximum after a total of three such iterations. This method allows assembling proteons in large quantities within an hour. In contrast, it takes much longer to produce just a minute quantity of these particles prepared by other methods.

Method of Replication of Proteons Obtained from Blood (Vodyanoy, et al., 2002).

Freshly drawn blood (30 μl) from healthy male subjects (human, rabbit and dog) was diluted to 1 ml with purified water in a 1.5-ml plastic tube and centrifuged at 13,000×g for 5 min at room temperature. The plasma supernatant was used to prepare both proteons and PNCs. To produce proteons, the supernatant was transferred to a 4-ml glass vial with a plastic cap with a Teflon liner and subjected to 120° C. at 140 kPa for 2 h. The fresh suspension (filtrate) was obtained by filtering the plasma supernatant consecutively through 30- and 5-kDa CENTRICON™ filters (Millipore Corp.). Shark's blood (Atlantic Sharpnose Shark, Rhizoprionodon terraenovae) contains approximately 5-fold more PNCs/ml than dog's or rabbit's blood (New Zealand white rabbit from Harland Sprague-Dawley).

PNC Preparation from Dog Blood.

Ten (10) ml of blood was diluted in 150 ml of water and centrifuged at 13,000×g for 40 min at 4° C. The pellet was discarded and supernatant was filtered through 5 layers of coffee filters. The supernatant was filtered successively through 30,000 D and 5,000 D CENTRICON PLUS-80™ Centrifugal Filter Devices (Millipore Corp.) by centrifugation at 3500×g for 40 min at 15° C. The filtrate was evaporated on a hot plate and then burned in a crucible at 650° C. for 1.5 hours. The remaining ash was then suspended in 15 ml of purified water, sonicated for 5 min, and further homogenized in a high speed homogenizer (Kinematica GmbH, Polytron, Switzerland) for 1 min. The suspension was centrifuged at 5445×g for 10 min at 15° C. The supernatant was filtered successively through 1.2, 0.8 and 0.22 μm filters (Millipore Corp.). pH of the preparation was adjusted to 7.8, sterilized in an autoclave at 120° C., and 20 psi for 20 min and stored in a refrigerator.

PNC Preparation from Frozen Atlantic Sharpnose Shark (Rhizoprionodon terraenovae) Tissue.

200 g of tissue were cut into small pieces and homogenized in a blender in 300 ml of purified water for 5 min. The homogenate was centrifuged at 13,000×*x* g for 40 min at 40° C. The pellet was discarded and the supernatant was filtered through 5 layers of coffee filters. pH of the supernatant was 6.5. The supernatant was filtered successively through 30,000 D and 5,000 D CENTRICON PLUS-80™ Centrifugal Filter Devices (Millipore Corp.) by centrifugation at 3500×g for 40 min at 15° C. pH of the filtrate was 6.2. The filtrate was evaporated on a hot plate at 95° C. and then burned in a crucible at 650° C. for 1.5 hours. The remaining ash was then suspended in 15 ml of purified water, sonicated for 5 min, and further homogenized in a high speed homogenizer (Kinematica GmbH, Polytron, Switzerland) for 1 min. The suspension was centrifuged at 5445×g for 10 min at 15° C. The supernatant was filtered successively through 1.2, 0.8 and 0.22 pm filters (Millipore Corp.). The filtrate was sterilized in an autoclave at 120° C., and 20 psi for 20 min. A. white precipitate that formed during autoclaving was removed by centrifugation at 5445×g for 10 min at 15° C. and subsequent filtration of the sample through a 0.22 μm filter (Millipore Corp.). pH of the sample was adjusted to pH 7.8 and stored in a refrigerator.

Proteons.

There are a few forms of proteons observed by the optical dark-field (Vodyanoy and Neely 2002), the transmission electron microscope (TEM), and scanning electron microscope (SEM). Type I proteons are largely presented by small particles of spherical shape of 50-250 nm. (FIGS. 1A and 1B). In the optical dark-field of the liquid samples, proteons look like fast randomly moving bright dots. TEM images show small proteons as dark discs (FIGS. 1A and 1B). FIG. 1A shows small proteons in the area of about 100 square microns, and FIG. 1B depicts proteons in a magnified small area of about 0.7 square microns. An analysis of TEM images revealed the size distribution of proteons with a maximum about 150 nm. Another form of proteons (type 2), coconut shape particles of about 1-5 microns with one or many nuclei are also observed by TEM (FIGS. 1C to 1G). A characteristic feature of this type 2 proteon is a cell-like appearance (FIG. 1C). The proteon has a very distinctive external membrane-like structure. This membrane-like structure, however, looks very different from the bacterial wall or the mammalian cell membrane. This external structure looks like a curly fibrous shell of 10-12 nm thick. Some fiber-like structures and a few nuclei are visible inside the proteon. More distinguished nuclei are visible inside the proteon shown in FIG. 1D and a proteon containing many nuclei are depicted in FIG. 1E. In the last case the proteon of type 2 looks open and expelling its nuclei. These nuclei look very similar to the small proteons of type 1. The type 2 proteon observed with TEM looks very similar to that found by SEM (FIG. 1G). The large coconut-shape proteon with a large opening is positioned on a bed covered with small type 1 proteons. We believe that proteons viewed by the electron microscopy are not artifacts of sample preparation, because similar images were obtained by two different EM techniques and by the optical dark-field microscopy where samples of proteons were not subjected to any physical or chemical treatments.

One more representative structure was always observed with practically all samples of proteons. The fibrous or filamentous structures were observed by all techniques. These structures are presented in a great variety of shapes and forms. They are seen as shapeless bundles filling the space between the proteons and they are structured into the outer shells and inside of large proteons (FIG. 1C).

Number of Proteons.

The fresh full blood sample contains approximately $3\times10^8$ proteons/ml visible with a darkfield microscope. After dilution and centrifugation, the sample contained $\sim9\times10^6$ proteons/ml. After the heat and pressure treatment the count of particles in the dark field shows a tremendous increase of number of suspended and moving particles estimated as $\sim3\times10^{11}$ proteons/ml. If this number is adjusted for the initial dilution of the blood sample, it will become $\sim1\times10^{13}$ proteons/ml. Thus, within two hours the number of proteons increased by approximately 5 orders of magnitude. The time during which the population of proteons is doubled, 8 minutes, is much smaller compared to the few days or over a week observed by using other methods (Kajander, 1992, Lindner and MacPhee, 2001).

The chemical composition was determined by energy dispersive X-ray spectroscopy using JEOL JSM-840 SEM system with an Oxford instruments ultrathin window (UTW) X-ray detector and an Oxford ISIS analyzer. The sample of proteons suspended in distilled water was deposited on the aluminium SEM mount and dried in a vacuum for 24 hours. The X-ray spectra were obtained with a probe current of about 1 nA at 20 kV with alive time of 60 s. When the beam was focused on the proteons, the resulting spectra revealed that proteons were composed of carbon, oxygen, nitrogen, and sulfur. We also found the presence of potassium, sodium, chlorine, zinc and copper.

Protein Concentration.

The quantitative analysis of proteins in the proteon samples was carried out by the assays obtained from BIO-RAD Laboratories. Samples of plasma were exposed to different temperatures and pressures. Results of the experiments are shown in Table 12A. We found that the number of proteons accounted for by dark-field microscopy is increased as temperature rises but the amount of protein remains the same.

TABLE 12A

| Sample, Condition | Protein concentration, µG/ml |
| --- | --- |
| Plasma, control, 25° C. | 0.67 ± 0.5 |
| Plasma, 56° C., normal pressure, 10 min | 0.72 ± 0.04 |
| Plasma, 80° C., normal pressure, 10 min | 0.68 ± 0.04 |
| Proteons, 120° C., 20 psi, 2 hours | 0.71 ± 0.04 |

There is No DNA in Proteons.

Two methods have been used to detect DNA in the samples. In the first method, the DNEASY™ Tissue Kit (Qiagen Corp.) was used to isolate and purify DNA. DNA was detected in plasma and undetected in proteon sample.

In the second method, HIGH PURE™ PCR Template Preparation Kit, (Roche Corp.) was used for isolation of nucleic acids. The fluorometic quantitation of double-stranded DNA was carried out with the PICOGREEN™ dsDNA Quantitation Reagent (Molecular Probes Inc.) using TECAN Spectrafluor Plus equipped with DeltaSOFT software for detecting fluorescence with excitation at 485 nm and emission at 535 nm. The results of the electrophoresis indicated the absence of DNA in the proteon sample. The result is confirmed by the fluorimetric quantitation.

| Sample | DNA conc. µG/ml |
| --- | --- |
| Blood | 45.1 |
| Plasma | 3.0 |
| Proteons, freshly prepared | 0.033 |
| Proteons, 3 months old | <0.001 |

Proliferation of Proteons.

The number of proteons incubated at 37° C. in purified water in an atmosphere of ambient air measured by a dark-field light microscope (Vodyanoy, et al., 2002) did not change significantly ($p<0.01$) during 13 days. The plasma at the same conditions showed a very small increase in population of proteons within 8 days of incubation, but the number increased dramatically and reached the number of proteons in group 1 after 13 days of incubation. Proteons and plasma in the tissue culture media (D5648 and D6429, respectively) showed the same proliferation curves and reached the same number of proteons after 13 days of incubation (FIG. 5). The culture media alone incubated at the same conditions show no increase in population of proteons (FIG. 5).

Reversibility of Assembling and Disassembling of Proteons in Vitro.

To examine the hypothesis of polymerization as a major mechanism in the construction of proteons, we exposed our samples to chaotropic compounds known to unfold and denature proteins: guanidine hydrochloride and urea. The samples of plasma were combined with the guanidine hydrochlorine or urea at concentrations of 0, 0.01, 0.1, 1, 4, and 8 M. The samples were subjected to heat of 120° C. and pressure of 20 psi. The number of proteons was decreased as concentration of chaotropic compounds was increased (FIG. 6). When samples of proteons replicated at the suppressive presence of 9 M urea were subjected to dialysis, the number of proteons increased significantly (FIG. 5, a data point labeled by a star). This experiment is consistent with the idea of nucleation and grows with the assistance of the nucleation centers (seeds). During the initial incubation in the presence of chaotropic compounds, the number of visible proteons was limited due to inhibited action of the compounds. When the chaotropic compounds were removed, the misfolded proteins were polymerized onto the preexisting seeds. These experiments provide methods of assembling and disassembling of proteons in vitro.

Protein Composition of Proteons Produced from Plasma.

Rabbit blood proteons were disassembled using the negatively charged detergent sodium dodecyl sulfate (SDS), and subsequent denaturing polyacrylamide gel electrophoresis revealed distinct protein bands of 14.4 and 8 kDa. N-terminal amino acid sequencing of both fragments yielded a partial sequence, which is 100% identical to a sequence within the rabbit Hb α-chain (Vonehren, 1966). Protein fragments from proteons were isolated by SDS-polyacrylamide gel electrophoresis, and identified by amino acid sequencing (University of Alabama Protein Analysis Laboratory). Amino acid analysis showed that, relative to rabbit Hb, proteons are enriched in the negatively charged residues glutamic acid and aspartic acid. Staining of proteons with congo-red resulted in apple-green birefringence under polarized light (Kelly, 1996), indicating the anisotropic alignment of dye molecules, which is similar to that observed with prions (Korth et al., 1997).

Methods of Amplification and Detection of Proteons

1. Single Step Amplification.

The test sample containing a small amount of misfolded proteins is subjected to a single heating step. The amplified number of proteons measured by dark-field microscopy and verified by immune fluorescent techniques justifies the detection of the misfolded protein. To increase the sensitivity of the single step methods, a small amount of seeds can be added to a test sample. Seeds obtained from proteons or metals known to promote a specific misfolding can be used for seeding (Armstrong et al., 2001; Bush et al., 1994; Esler at al., 1996; Johnston at al., 1999, 2000; Maggio et al., 1995; Mantyh at al., 1993; Minton, 2000; Mocchegiani et al., 2001; Attwood, 2002; Campbell at al., 2001). A temperature as low as 50° C. or lower and a heating step of 5-10 minutes can be used, and thus no special equipment is needed.

2. Cyclic Amplification.

After the first step amplification described above, the small portion of amplified sample is introduced in the untreated sample and subjected to heat again. Then, the small portion of the second amplified sample is added to the third untreated sample, heated and so on. The whole procedure can be carried out using a regular laboratory multi well heater. The first two cycles result in a small but significant increase of proteon population, whereas the third cycle brings about a dramatic increase in the number of proteons. The next three cycles result in saturation of the proteon population. Samples for the cyclic amplification can be prepared from homogenates of small tissue fragments, or better from blood, cerebrospinal, lymphatic, and other fluids. (Brown, at al., 2001; Aguzzi, 2000; Aguzzi, 2001; Wadsworth, at al., 2001). The cyclic amplification procedure developed in this work takes less than an hour. In contrast, the procedure offered by Saborio, 2001 takes from 5 to 40 hours.

Seeds, Proteon Nucleating Centers (PNCs)

Hypothesis

Metal clusters (Gonzalez-Morega, 1993; Aiken & Finke, 1999) play a role in the seeds in proteons, Metals involved in the natural folding and misfolding of proteins are not in the ion state, but rather in the clusters of metal atoms. These atoms are directly bonded to each other creating a polyatomic metallic nucleus that can exist alone or are associated with a given number of ligands.

Rationale:

The most remarkable property of metal clusters is that they provide a binding template for folding and aggregation of proteins (Liu and Xu, 2002). High symmetry is one of the main characteristics of metal clusters (Gonzalez-Moraga, 1993). Packing of secondary structures prefers geometrical patterns (Gracy et al., 1993; Onuchic et al., 1997). Many disorders arise from misfolding and aggregation of an underlying protein (Carrel and Lormas, 1997; Sato, 2001). The same disorders were shown to depend on metal misbalance (Bush, 2000). Copper, iron or manganese are involved in the aging and neurological disorders. Metals are involved in prion diseases (Lehman, 2002, Thackray, et al., 2002). Among 327 possible protein folds (Chothia, et al., 1997) only 230 folds are unique. The number of unique space groups applied to inorganic clusters is also equal to 230! (Hahn, 1987). The mathematical accuracy and stability of geometrical patterns and a large number of structural arrangements of metal clusters make them uniquely qualified as perfect templates for protein folding.

Experimental Evidence:

When PNCs were removed from blood plasma by filtration through a 5-kDa filter, the amount of protein in the retentate was equivalent to that of the non-filtered sample, and no protein was found in the filtrate (data not shown). Proteons could not be produced from the retentate until an aliquot of the filtrate was added back, and proteon production was dependent on the amount of filtrate added (data not shown). Interestingly, proteons cound be produced in this matter even after the filtrate was carbonized at 660° C., but production was quenched by 10 mM EDTA, and a metal-chelating agent (data not shown)(Irving and Al-Jarrah, 1975). Adsorption spectra (GTW Analytical Services) of the filtrate revealed the presence of metals, namely Cu, ZN and Fe (data not shown).

TEM showed that the bulk of the drived PNC-containing filtrate was amorphous, and that it contained crystalline metallic nanoparticles 1-2 nm in diameter. Selected area diffraction (SAD) patterns from different regions of the samples were consistent with both face-centered cubic (FCC) and body centered cubic (BCC) metals. Furthermore, both copper and iron were identified from EDS spectra acquired from regions containing the nanoparticles (data not shown) that the diffraction patterns were not consistent with an organometallic structure number of metal atoms. For example, the volume of a 1 nm diameter Cu particle is approximately equivalent to 10 Cu (or 20 α-Fe) unit cells (Borchardt-Ott, 1993). Given that FCC and BCC metals contain four and two atoms per unit cell, respectively (Borchardt-Ott, 1993), there data suggest that a particle containing ~40 atoms is formed regardless of the lattice type. Furthermore, the very fact that the metallic nanoparticles exist implies that the environment in which they formed prevented both oxidation and coarsening of the particles.

Proposed Role of PNCs

PNCs consist of 1-2-nm metal nanoparticles that contain 40-300 atoms. Given that proteons contain both PNCs and fragments of the Hb α-chain (see FIG. 1C), we conclude that PNCs play an important role in capturing Hb released to blood plasma. Released Hb is normally captured by haptoglobin, which is then recognized by Hb scavenger receptors and endocytosed by macrophages (Kristiansen et al., 2001). We speculate that when haptoglobin is depleted during critically elevated hemolysis (Delss, 1999), released Hb is collected by PNCs. We estimate that about $7 \times 10^{13}$ PNCs/ml are present in human blood, and that only about 0.004% of the entire PNC pool is normally linked to proteins to form proteons. On average, a 160-nm diameter proteon can bind about 100,000 protein molecules that are the size of Hb. TEM data indicated that blood contains abundant copper nanoparticles, suggesting that proteons result from the nucleation and growth (Eaton and Hofrichter, 1990) of misfolded Hb on copper PNCs. This process may offer insights into the mechanisms of some blood disorders associated with intravascular hemolysis, which results in Hb aggregation (Kannan et al., 1988; Schluter and Drenckhahn, 1986; Papalexis et al, 2001). Indeed, copper plays a critical role in other protein conformation-based disorders such as prion disease, Parkinson's disease, Alzheimers disease and familial amyotrophic lateral sclerosis (Brown et al., 1997). Metal clusters in blood may have many other functions. We were surprised to discover that small concentrations of PNCs were lethal to cultured cancer cells, whereas non-cancerous cells were much less affected (Samaylov et al., 2005).

Small metal nanoclusters meet requirements to serve as nuclei for aggregation of proteins and their fragments: i.e. Small, a few nm or smaller; Large quantity, about $10^{13}$ PNCs/$cm^3$ of blood or tissue; Abundant source for replenishing; Binding sites and strong affinity to proteins; Variability to bind different proteins; Stability to resist extreme physical and biochemical conditions (high temperature, pressure, acid and alkaline environments, oxygen, organic solvents, detergents, antibiotics, proteases, lipases).

Comparison with Nanobacteria

The presence of nanobacteria in blood was reported by Kajander, 1992, Kajander and Ciftcloglu, 1998. We carried out experiments to compare proteons and nanobacteria of Kajander. We use Nanocapture ELISA (Nanobac OY, Finland) for detection of nanobacterial antigens. The nanobacteria included in the Nanocapture ELISA were used as a positive control. Nanobacteria gave a very strong signal, while all freshly prepared proteons showed no interaction. All proteons incubated in cell culture media for 13 days, at 37° C. (with and without $CO_2$) have shown a positive reaction. The culture media alone incubated for 13 days, at 37° C. gave also a positive reaction, while freshly prepared culture media was negative, indicating that nanobacteria antigen appeared from the culture media during the incubation. The most likely source of nanobacteria proteins is the FBS added to each culture media (Kajander and Ciftcioglu, 1998).

Proteons from Yeast Extract

In order to produce proteons from yeast extract (BBL Yeast Extract from *Saccharomyces cerevisiae*, Difco laboratories) the extract at concentration of 100 mg/ml was dissolved in purified water and centrifuged at 13,000×g for 40 min at 4° C. Supernatant was sterilized at 120° C., 20 psi for 20 min. In the optical dark-field of supernatant we observed large number of particles that look like fast randomly moving bright dots similar to those observed in blood plasma. The transmission electron microscope revealed the presence of particles with very similar structure to those discovered in human, dog, rabbit, and shark blood. Negatively stained particles from yeast extract demonstrated the presence of one or several dark nuclei. We speculate that these particles are proteons. Staining of yeast proteons with Congo red resulted in apple-green birefringence under polarized light, indicating the anisotropic alignment of dye molecules similar to that observed with proteons from human blood and prions (Korth et al., 1997). Protein composition of proteons produced from yeast extract needs to be determined to identify the nature of the particles. We do not have high expectations to find any yeast prion proteins in these particles because in contrast to the mammalian prion proteins they are not known to be metal dependent (Bousset and Melki, 2002). It is also motivating to determine if the yeast prion proteins interact with PNCs obtained from the yeast extract.

PNCs from Yeast Extract

PNCs from dry yeast extract were prepared following the protocol similar to one used for preparation of PNCs from animal blood. Briefly, the extract at concentration of 100 mg/ml was dissolved in purified water and centrifuged at 13,000×g for 40 min at 4° C. After the pellet was discarded the supernatant was filtered successively through 30,000 D and 5,000 D CENTRICON PLUS-80™ Centrifugal Filter Devices (filters (Millipore Corp.) by centrifugation at 3500×g for 40 min at 18° C. The filtrate obtained after two rounds of filtration was autoclaved at 120° C., and 20 psi for 20 min The sample was evaporated on a hot plate and then burned in a crucible at 650° C. for 1 hour. The remaining ash then was suspended in water, sonicated for 5 min, and filtered through a 0.8 pm filter (Millipore Corp.). The obtained material was arbitrarily termed yeast PNCs until further structural and functional characterization. Metals in yeast PNCs were identified by inductively coupled plasma-atomic emission spectrometry (GTW Analytical Services, USA), The yeast PNCs contain abundant metals, among which are iron (0.157 mg/l), zinc (0.507 mg/l, and magnesium (1.1 mg/l). Preliminary results show that yeast PNCs have similar functional properties to those obtain from blood.

Proteons from Prion Protein (PrP)

Recombinant human PrP(23-230) was purchased from Alicon company (Switzerland). One hundred micrograms of the protein were dissolved in purified water at concentration of 1 mg/ml at 25° C. In the optical dark-field the liquid untreated samples revealed randomly moving particles, similar to those observed in blood. No sediment was found on the slides. When PrP was subjected to 120° C. at 20 psi for 20, min the number of moving particles decreased compared to the untreated sample and sediment was observed on the slide. When 3 μl of PNCs suspension from shark at concentration of $5 \times 10^{18}$/mL were added to 7 μl of PrP solution and the sample was heated at 120° C. at 20 psi for 20 min a very large number of extremely small particles was observed with a darkfield microscope. The number of small particles was many times higher than that observed without PNCs. Additionally, large sediments were formed on the glass surface.

The transmission electron microscope (TEM) showed a few types of structures in PrP samples. In samples without PNCs we observed a very small number of relatively large round ball type particles of about 300 nm and very small number of particles of about 30 nm. If PNCs were not added to the PrP solution we did not find any filamentous or fiber like structures. In the presence of PNCs after 15 minutes of the heat treatment we observed a dramatic change in the protein structure. A large number of small particles (arrow) of about 10-15 nm and filamentous structures were produced in the presence of PNCs. It appears that these particles were converted first in the thin short rodlets (40-50, nm long) and then the rodlets were interconnected into longer thin filaments. After that thin filaments were interwoven into the thicker fibril looking like a rope with fibers. Finally, large fibrils were creating a complicated system of fibrils and plaques.

The critical step in the prion transformation is the conversion of monomeric prion protein with a mainly α-helical structure into multimeric misfolded prion protein. which has predominantly a β-sheet structure (Wisniewski, et al. 1998). The final products of this conversion are amyloid fibrils and amyloid plaques that cause prion diseases. In vitro transition of recombinant fragments of PrP into aggregated structures has been reported for different species (Wille et al., 2002; Kuwata et al., 2003; Sokolowski et al., 2003). The aggregation process of recombinant Syrian hamster prion protein was found to be accompanied by formation of small oligomers aggregated into spherical particles of 10-15 nm and short rodlets of about 40-50 nm (Sokolowski et al., 2003; Modler et al., 2004). Similar fibrillar structures were observed by Kuwata et al., 2000 for the human prion protein fragments, PrP106-126. As was indicated by these studies, the longer time of grow was characterized by an increased length of fibrillar structures. Structural features of prion particles observed in our work are fully consistent with those found for the hamster and human prion fragments, with the difference that we were able to produce these structures much faster. It took a strong denaturant, 1 M guanidine hydrochloride at pH 4.2, and 25 days to grow 10-15 nm particles and 55 days to grow relatively short filaments from the hamster PrP (Sokolowski et al., 2005), while it took us only 15 minutes. We attribute the difference in the rate of growth to the presence of PNCs and elevated temperature, so that prion particles formed by seeded aggregation of proteins around nucleating centers. It was shown that prion protein oligomers generated at low and elevated temperatures did not exhibit any significant differences in secondary structure (Sokolowski et al., 2005), but the elevated temperatures alone cannot produce the rate of growth of prion fibrils comparable with that of our experiments.

What Prions are Proteons?

Proteons and prions share many physical and chemical properties. They both are misfolded proteins, polymorphic, have no nucleic acids, metal dependent, and very resistant. They both may be induced by seeds and be controlled by guanidine hydrochloride. They both play a certain role in a cell death. They both have the same proliferation rate at 37° C. (Aguzzi and Heppner, 2002; Everbroeck, et al., 2002; Ness, et al., 2002; Bounias and Purdey, 2002; Gemer 1997, 2002). Our experiments with the recombinant human protein described in the section "Proteons from prion protein (PrP)" suggest that metal nanoclusters (PNCs) play important role in production of prion particles. We need to present experimental evidence that metal particles are indeed inside the prions particles. In order to make a statement that naturally occurring prions are proteons, that is to say, natural prion particle is the misfolded prion protein aggregated around non-organic nanoparticle that serves as a nucleating center, it would require to analyze prions obtained from the animal with the prion disease. There is substantial evidence that PrP is a Cu-binding protein. It is suggested that in conversion to the abnormal form the Cu-binding activity is switched to the binding other metals such as Mn or Zn (Brown, 2004). In this work we do not plan to work with prions obtained from animals with prion diseases. We will work with in vitro system of prion particles produced from the recombinant human PrP(23-230) protein and metal PNC and examine if these particles have acquired the ability to convert the normal form of the protein into this same abnormal (prion) form.

D. Research Design and Methods

Research Strategy

This experiment was conducted as follows: 1) first, perform assay of proteon amplification at different physical and chemical conditions. Data obtained in the experiments are utilized to determine conditions controlling assembling and disassembling of protein particles (proteons). 2) separate nuclei and proteins by chemical and physical methods; determine structure and composition of protein particles and PNCs by electron microscopy techniques, energy dispersive X-ray spectrometry, and X-ray diffraction, Seeds (PNCs) purified from plasma and artificial PNCs (metal nanoparticles) are to be used to control assembling of proteons. Experiments in the present project deal with small particles, using materials and methods, which have been successfully examined in our laboratories. It takes approximately 18 months to carry out and analyze experiments related to each specific aim.

Aim 1. In this portion of the experiment we will determine conditions controlling assembling and disassembling of protein particles (proteons). The main hypothesis of this aim is that the stable inorganic nuclei control misfolding and aggregation of prion-related proteins. The rationale that underlines this aim is that our preliminary results together with literature data strongly indicate that seeded polymerization and aggregation is an important mechanism of replication of prions, among other misfolded proteins. The seeds (PNCs) are very resistant to various physical and chemical factors. The process of amplification of misfolded proteins is sensitive to the microenvironment of interacting protein and PNCs. The strategy will be to characterize the influence of the microenvironment on the kinetics of replication and properties of proteons using our in vitro amplification method. The particles will be characterized by dark-field light and electron microscopy and identified by gel electrophoresis and immunoblotting. The kinetic data will be analyzed with the theoretical nucleated polymerization model and will be compared with known results of prion replication and proliferation of other protein aggregates.

Experimental Design.

We will accomplish the objective of this aim by conducting the following experiments:

Experiment a:

Perform assay of proteon amplification at different physical and chemical conditions:

(1). Temperature at the range of 30-120° C., normal pressure at temperatures below 100° C., and elevated pressures up to 20 psi at the temperatures between 100 and 120° C., different time of assay. This experiment determines the effects of temperature and pressure on the assembling and disassembling of proteons. It has been clearly demonstrated that temperature and pressure are important factors in the stability of proteins (Smeller, 2002). Changes in protein amino acid composition or microenvironment may cause destabilization of protein. Although, it is important that correctly folded and misfolded prion protein do not differ in their amino acid sequence. Prion disorders are such diseases where destabilized proteins form insoluble fibers (Fink, 1998, Booth, et al., 1997). Interaction between protein and PNC can bring a protein in the metastable state, which is prone to aggregation (Smeller et al., 1999). The amplification of the proteons will be carried out as described in the method section.

(2) Other factors effecting stability of proteins in blood. Because this work targets a blood diagnosis and involves proteins from blood some factors which can affect stability of proteins in blood need to be considered. The concentration of hydrogen ions (pH) is an important factor of protein stability (Smeller, 2002). Reactive oxygen species (ROS) available in blood cause oxidative protein damage (Alayash, et al., 2001). Neutrophils secrete considerable amount of hydrogen peroxide and hypochlorous acid (Chatham, et al., 1994).

(3) Natural and artificial PNCs. We have demonstrated in that addition of minute quantities of proteins in plasma can dramatically enhance proliferation of proteons. We will examine effect of PNCs when they are available in the Aim 2.

(4) Chaotropic compounds, such as guanidine hydrochloride and urea are shown to disassemble proteons. It is consistent with results of Ness, et al., 2002, who demonstrated that guanidine hydrochloride inhibits the generation of prion "PNCs" in yeast. It has been also demonstrated that critical oligomers necessary for production of prion particles can be generated by incubating the prion protein in I M guanidine hydrochloride (Sokolowski et al., 2003; Sakolovski and Naumann, 2005).

(5) chelating agents such as EDTA, EGTA, and EDPA form strong complexes with metals and they will be used to control stability of proteons and characterize interaction of PNCs and proteins (Kaushik and Shat 1999).

(6) Inhibitory compounds like creosote. In our preliminary experiments we observed that addition of small concentration of creosote stops the motility of proteons and make them disappear from the optical dark-field microscope image (data not shown). Creosote contains many polycyclic aromatic hydrocompounds (Nylund, et al., 1992) and was known from antiquity for preservation of wood and food products (Phillips, 1999).

(7) Protective compounds, like trehalose, sucrose and raffinose are natural protective compounds which cells use as defenses against unfolded proteins (Sherman and Goldberg, 2001). Under this Experiment, we will have a better understanding of process and optimal conditions of assembling and disassemmbling of proteons and will be able to control replication of misfolded proteins in vitro.

Experiment b:

Perform assay of cyclic proteon amplification at 65° C. with addition of natural and artificial PNCs. The cyclic amplification of proteons in plasma is carried out as it was described in preliminary results. The natural and artificial PNCs are added to accelerate the assembling of proteons. The PNCs will be prepared and analyzed as described in the Aim 2. We expect to tune temperature and PNC's quality and concentration to optimize the assembling of proteons. The obtained information, from Experiment b, when combined with results of Experiment a, the method of cyclic amplification can be turned into an efficient method of mass production of misfolded proteins in plasma needed for diagnostics. Proteins from blood for cyclic amplification were used as described in the section "Methods of amplification and detection of proteons" of Preliminary Studies. Proteins from yeast for cyclic amplification were obtained from yeast extract (BBL Yeast Extract from *Saccharomyces* ceravilskC Difco laboratories) as described in section "Proteons from yeast extract" of Preliminary Studies. The human prion protein is expressed in and purified from *E. coli* cells as described by Zahn at al (1997).

Aim 2. In this Aim we Define and Characterize Properties of Nuclei (PNCs) Participating in Misfolding, Polymerization, and Aggregation of Proteins.

The main hypothesis is that metallic or inorganic compound acts as nucleus for misfolded proteins. The rationale that underlines this aim is discussed in the subsection "PNCs" of the Preliminary results. The essence of the concept is that the metal site works as a template for the metal/protein structure formation (Liu and Xu, 2002).

Experimental Design.

We accomplished the objective of this aim by conducting the following experiments:

Experiment a:

Separate nuclei and proteins by chemical and physical methods: SDS polyacrylamide-gel electrophoresis. The idea of this experiment is to disassemble proteons by a negatively charged detergent, SDS, and then to electrophorese down stripped proteins leaving heavier PNCs on the top of the band. Recovered PNCs than can be analyzed. In our preliminary work we demonstrated that SDS could disassemble proteons and proteins are electrophoresed (data not shown). Chelating resin column (Sigma Inc., CHELEX-100™ brand, 50-100 mesh) is a standard laboratory technique of extracting metals (Vidal, et al, 2002). Chaotropic compounds are commonly used for a liquid extraction of polyvalent metals (Nash and Horowitz, 1990). Dry ashing with an electric furnace, microwave, and oxygen plasma is used to mineralize and then to extract an inorganic component from proteons (Vidal, et al., 2002).

Experiment b:

determine structure and composition of protein particles and PNCs by electron microscopy techniques, X-ray spectrometry and X-ray diffraction. TEM techniques include bright field (BF) imaging of unstained samples, or which a large image contrast would be present between the crystalline metallic particles (producing diffraction contrast) and the amorphous protein background (producing only mass—thickness contrast). TEM BF imaging is supported by extensive electron diffraction studies, which would be used to confirm the crystal structure (Bravais lattice) of the particles. Nanobeam diffraction (NBD) would be employed to obtain single crystal type patterns from individual particles and selected area diffraction (SAD) will be used to characterize particles an-masse. TEM DF imaging would be utilized to allow the association of features of the diffraction patterns with specific portions of the specimen. TEM-based energy-dispersive X-my spectroscopy (EDS) will provide chemical composition information and this will compliment the structural information provided by the diffraction studies. The PNCs and proteins will be separated as described in Experiment a and characterized by EDS in the scanning electron microscope (SEM) and X-ray diffraction (XRD). (Porter and Easteding, 1992; Murr, 1975)

Experiment c:

Prepare PNCs purified from plasma and artificial PNCs using information obtained in Experiment b of Aim 2; use metallic nanoparticles as model systems. We prepared purified PNCs from plasma using the same methods of separation of PNCs and proteins as described in the Experiment a (Aim 2). Metal nanoparticles can be obtained from Agronide Nanomaterials, FL. If proteons are formed with help of PNCs in blood and PNCs have certain physiological significance, then certain criteria of PNCs involvement in forming of proteons must be fulfilled: (i) blood should contain PNCs; (ii) proteons should be formed from proteins in vitro in the presence of PNCs; (iii) proteons should not be formed or formed at very low rate if PNCs are absent or blocked; and (iv) PNCs should mimic proteons in the process of conversion of protein into proteon. That criteria i-iv are met for Hb proteons and PNCs in blood was clearly demonstrated in our preliminary experiments (Samoylov, et al., 2005). These criteria will be applied to examine the in vitro system of prion protein/PNCs.

Innovations:

This Experiment demonstrates two major innovative components: the hypothesis about inorganic nature of PNCs inducing misfolding of proteins, and a new and very effective method of amplification or proliferation of misfolded proteins in vitro.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for isolating proteins from a plasma sample, the method comprising:
   a) adding to the sample isolated proteon nucleation centers (PNCs), the PNCs each comprising metal nanoclusters having average diameter of about 1-2 nm and containing about 40-300 metal atoms selected from the group consisting of copper, zinc, and iron;
b) heating the sample to increase proteons in the sample; and
c) isolating the proteons from the sample.

2. The method of claim 1, wherein the sample is heated for at least about 1, 5, 10, 15, 20, 25, 30, 35, 40, 45, 50, 55, 60, 65, 70, 75, 80, 85, 90, 95, 100, 105, 110, 115, or 120 minutes.

3. The method of claim 1, wherein the sample is heated to a temperature of at least 37, 40, 45, 50, 55, 60, 65, 70, 75, 80, 85, 90, 95, 100, 105, 110, 115, or 120° C.

4. The method of claim 1, further comprising applying pressure to the sample of at least 14, 15, 16, 17, 18, 19, 20, 21, 22, 23, 24 or 25 psi.

5. A method for isolating proteons from a plasma sample, the method comprising:
a) adding to the sample isolated proteon nucleation centers (PNCs), the PNCs each comprising metal nanoclusters having average diameter of about 1-2 nm and containing about 40-300 metal atoms selected from the group consisting of copper, zinc, and iron;
b) heating the sample to increase proteons in the sample;
c) repeating steps a) and b); and
d) isolating the proteons from the sample.

6. The method of claim 5, wherein steps (a) and (b) are repeated until the number of proteons formed in the sample no longer increases.

7. The method of claim 5, wherein the sample is heated for at least about 1, 5, 10, 15, 20, 25, 30, 35, 40, 45, 50, 55, 60, 65, 70, 75, 80, 85, 90, 95, 100, 105, 110, 115, or 120 minutes.

8. The method of claim 5, wherein the sample is heated to a temperature of at least 37, 40, 45, 50, 55, 60, 65, 70, 75, 80, 85, 90, 95, 100, 105, 110, 115, or 120° C.

9. The method of claim 5, further comprising applying pressure to the sample of at least 14, 15, 16, 17, 18, 19, 20, 21, 22, 23, 24 or 25 psi.

10. The method of claim 5, wherein the sample is heated for at least 15 minutes at a temperature of at least 65° C. and steps a) and b) are repeated at least six times.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Oryctolagus cuniculus

<400> SEQUENCE: 1

Val Leu Ser Pro Ala
1               5
```